(12) United States Patent
Stefano et al.

(10) Patent No.: US 6,524,805 B1
(45) Date of Patent: Feb. 25, 2003

(54) METHODS FOR IDENTIFYING ESTROGEN SURFACE RECEPTOR AGONISTS

(76) Inventors: George B. Stefano, 1 Sleepy La., Melville, NY (US) 11747; Caterinea Fimiani, Via Ceneda 39, 00183 Roma (IT)

(*) Notice: Subject to any disclaimer, the term of this patent is extended or adjusted under 35 U.S.C. 154(b) by 0 days.

(21) Appl. No.: 09/530,880

(22) PCT Filed: Nov. 10, 1998

(86) PCT No.: PCT/US98/23944
§ 371 (c)(1),
(2), (4) Date: Sep. 28, 2000

(87) PCT Pub. No.: WO99/24471
PCT Pub. Date: May 20, 1999

Related U.S. Application Data

(60) Provisional application No. 60/065,043, filed on Nov. 10, 1997.

(51) Int. Cl.[7] ................. G01N 33/53; G01N 33/567
(52) U.S. Cl. ............................ 435/7.2; 435/7.21
(58) Field of Search .................... 435/7.1, 7.2, 7.21; 530/350, 366

(56) References Cited

U.S. PATENT DOCUMENTS

| | | |
|---|---|---|
| 4,873,191 A | 10/1989 | Wagner et al. |
| 5,225,440 A | 7/1993 | London et al. |
| 5,580,859 A | 12/1996 | Felgner et al. |
| 5,589,466 A | 12/1996 | Felgner et al. |

FOREIGN PATENT DOCUMENTS

| | | |
|---|---|---|
| WO | WO 98/33937 | 8/1998 |

OTHER PUBLICATIONS

Bare et al., *FEBS Letters*, 1994, 354:213–216.
Bilfinger et al., *Ann. Thorac. Surg.*, 1997, 63(4):1063–1069.
Fox–Threlkeld et al., *J. Pharmacol. Exp. Ther.*, 1994, 268(2):689–700.
Gossler et al., *Proc. Natl. Acad. Sci. USA*, 1986, 83(23):9065–9069.
Iuvone et al., *Biochem. Biophys. Res. Comm.*, 1995, 212(3):975–980.
Lantin–Hermoso et al., *Am. J. Physiol.*, 1997, 273(1, Part 1):L119–L126.
Lo, *Mol. Cell. Biol.*, 1983, 3(10):1803–1814.
Magazine et al., *J. Immunol.*, 1996, 156(12):4845–4850.
Makman et al., *Adv. Exp. Med. Biol.*, 1998, 437:137–148.
Raynor et al., *J. Pharmacol. Exp. Ther.*, 1995, 272:423–428.
Sambrook et al., *Molecular Cloning—A Laboratory Manual*, 1989, 2$^{nd}$ Edition, Cold Spring Harbor Laboratory Press (Table of Contents only).
Schnieke et al., *Science*, 1997, 278:2130–2133.
Sedqi et al., *Biochem. Biophys. Res. Comm.*, 1995, 209(2):563–574.
Stefano et al., *Science*, 1981, 213(4503):928–930.
Stefano et al., *Proc. Natl. Acad. Sci. USA*, 1992, 89(19):9316–9320.
Stefano et al., *Proc. Natl. Acad. Sci. USA*, 1993, 90(23):11099–11103.
Stefano et al., *J. Biol. Chem.*, 1995, 270(51):30290–30293.
Thompson et al., *Cell*, 1989, 56:313–321.
Van Der Putten et al., *Proc. Natl. Acad. Sci. USA*, 1985, 82(18):6148–6152.
Vidal et al., *Immunopharmacology*, 1998, 38(3):261–266.
Wendel et al., *J. Mol. Med.*, 1998, 76:525–532.
Zhao et al., *Peptides*, 1996, 17(4):619–623.

*Primary Examiner*—Gary Kunz
*Assistant Examiner*—Robert S. Landsman
(74) *Attorney, Agent, or Firm*—Fish & Richardson P.C., P.A.

(57) ABSTRACT

The present invention relates generally to mu3 opiate receptors, cannabinoid receptors, and estrogen surface receptors (ESRs). Specifically, the invention provides methods and materials for identifying mu3 opiate receptor agonists and antagonists, cannabinoid receptor agonists and antagonists, and ESR agonists and antagonists. In addition, the invention provides an isolated nucleic acid molecule that encodes a mu3 opioid receptor, and an isolated mu3 opioid receptor polypeptide. Further, the invention provides methods and materials for treating cancers, inflammatory conditions, sepsis conditions, viral infections, and cardiovascular diseases.

15 Claims, 5 Drawing Sheets

SEQUENCE LISTING

<160> NUMBER OF SEQ ID NOS: 6

<210> SEQ ID NO 1
<211> LENGTH: 20
<212> TYPE: DNA
<213> ORGANISM: Homo sapiens

<400> SEQUENCE: 1
gcagaggaga atgtcagatg                                           20

<210> SEQ ID NO 2
<211> LENGTH: 20
<212> TYPE: DNA
<213> ORGANISM: Homo sapiens

<400> SEQUENCE: 2
ctaagcttgg tgaaggtcgg                                           20

<210> SEQ ID NO 3
<211> LENGTH: 30
<212> TYPE: DNA
<213> ORGANISM: Homo sapiens

<400> SEQUENCE: 3
ggtactggga aaacctcgtg aagatctgtg                                30

<210> SEQ ID NO 4
<211> LENGTH: 30
<212> TYPE: DNA
<213> ORGANISM: Homo sapiens

<400> SEQUENCE: 4
ggtctctagt gttctgacga attcgagtgg                                             30

<210> SEQ ID NO 5
<211> LENGTH: 441
<212> TYPE: DNA
<213> ORGANISM: Homo sapiens

<400> SEQUENCE: 5
ggtactggga aaacctgctg aagatctgtg ttttcatctt cgccttcatt atgccagtgc    60
tcatcattac cgtgtgctat ggactgatga tcttgcgcct caagagtgtc cgcatgctct   120
ctggctccaa agaaaaggac aggaatcttc gaaggatcac caggatggtg ctggtggtgg   180
tggctgtgtt catcgtctgc tggactccca ttcacattta cgtcatcatt aaagccttgg   240
ttacaatccc agaaactacg ttccagactg tttcttggca cttctgcatt gctctaggtt   300
acacaaacag ctgcctcaac ccagtccttt atgcatttct ggatgaaaac ttcaaacgat   360
gcttcagaga gttctgtatc ccaacctctt ccaacattga gcaacaaaac tccactcgaa   420
ttcgtcagaa cactagagac c                                             441

<210> SEQ ID NO 6
<211> LENGTH: 146
<212> TYPE: PRT
<213> ORGANISM: Homo sapiens

<400> SEQUENCE: 6

Tyr Trp Glu Asn Leu Leu Lys Ile Cys Val Phe Ile Phe Ala Phe Ile
 1               5                  10                  15

Met Pro Val Leu Ile Ile Thr Val Cys Tyr Gly Leu Met Ile Leu Arg
            20                  25                  30

Leu Lys Ser Val Arg Met Leu Ser Gly Ser Lys Glu Lys Asp Arg Asn
        35                  40                  45

Leu Arg Arg Ile Thr Arg Met Val Leu Val Val Val Ala Val Phe Ile
    50                  55                  60

Val Cys Trp Thr Pro Ile His Ile Tyr Val Ile Ile Lys Ala Leu Val
 65                  70                  75                  80

Thr Ile Pro Glu Thr Thr Phe Gln Thr Val Ser Trp His Phe Cys Ile
                85                  90                  95

Ala Leu Gly Tyr Thr Asn Ser Cys Leu Asn Pro Val Leu Tyr Ala Phe
            100                 105                 110

Leu Asp Glu Asn Phe Lys Arg Cys Phe Arg Glu Phe Cys Ile Pro Thr
        115                 120                 125

Ser Ser Asn Ile Glu Gln Gln Asn Ser Thr Arg Ile Arg Gln Asn Thr
    130                 135                 140

Arg Asp
145

METHODS FOR IDENTIFYING ESTROGEN SURFACE RECEPTOR AGONISTS

RELATED APPLICATION

This application is a U.S. National Phase application of PCT Patent Application No. PCT/US98/23944, filed Nov. 10, 1998, which claims benefit from U.S. Provisional Patent Application No. 60/065,043, filed Nov. 10, 1997, now abandoned.

STATEMENT AS TO FEDERALLY SPONSORED RESEARCH

Funding for the work described herein was provided by the federal government under Grant No. 5R24 DA 0901007, which may have certain rights in the invention.

BACKGROUND

1. Technical Field

The invention relates to methods and materials involved in the activation and inhibition of opiate, cannabinoid, and estrogen receptors. Specifically, the invention relates to mu3 opiate receptors, cannabinoid receptors, and estrogen surface receptors, and the biological responses induced by such receptors.

2. Background Information

Three general classes of cell surface opioid receptors (kappa, delta, and mu) have been described based on ligand specificity. Opioid receptors exhibiting high binding specificity for morphine have been designated mu opioid receptors. Detailed analysis of mu opioid receptors from various tissue has revealed the existence of multiple mu opioid receptor subtypes. In fact, the cDNA encoding the mu1 opioid receptor subtype has been identified. Oligonucleotides complementary to some, but not all, exons of the mu1 opioid receptor can block the effects mediated by the mu1 and mu2 receptor subtypes. Thus, the mu1 and mu2 opioid receptor subtypes appear to share exon sequences, as would be expected of splice variants. Supporting the idea of alternative splicing is the finding of a single mu gene in mouse chromosomal DNA. In addition, a novel rat brain mu opioid receptor subtype, designated rMOR1B, has been identified. This receptor is identical to the rat mu1 opioid receptor at its N-terminus but differs in its length and sequence at the C-terminus. Further, affinity studies demonstrated that the substrate specificity of rMOR1B is similar to that of the rat mu1 opioid receptor, but rMOR1B is more resistant to agonist-induced desensitization and has a different expression pattern in brain. The presence of another opiate receptor, designated mu3 opiate receptor, has been demonstrated pharmacologically. This mu3 opiate receptor is opioid peptide insensitive and opiate alkaloid selective. In addition, detailed binding analysis indicates that the mu3 opiate receptor is expressed by immune tissues (e.g., human monocytes and granulocytes).

Cannabinoids induce physiological activities similar to those induced by morphine. Cannabinoids, however, induce these activities by interacting with specific cannabinoid receptors that are structurally distinct from opioid receptors. To date, two subtypes of G-protein-coupled cannabinoid receptors have been identified: CB1 and CB2. These two cannabinoid receptor subtypes are expressed by different tissues and have different pharmacological properties. For example, the CB1 receptor is expressed in brain and endothelial tissue while the CB2 receptor is expressed in the immune system. In addition, SR 141716A is a CB1 receptor antagonist while SR 144528 is a CB2 receptor antagonist.

Estrogen, like morphine, appears to have multiple receptors. In fact, two different cDNA clones have been identified: one encoding estrogen receptor-alpha (ER-alpha) and the other encoding estrogen receptor-beta (ER-beta). In addition, many variants of ER-beta have been described, including human ER-beta isotypes 1 through 5. Unlike the mu opioid receptor subtypes, however, these estrogen receptors are intracellular nuclear receptors. Presumably, each of these intracellular estrogen receptors, upon interaction with estrogen, mediate biological responses by interacting directly with DNA. Tamoxifen is a lipophilic anti-estrogen compound that can inhibit the interaction of estrogen with intracellular nuclear receptors.

SUMMARY

The present invention relates generally to mu3 opiate receptors, cannabinoid receptors, and estrogen surface receptors (ESRs). Specifically, the invention provides methods and materials for identifying mu3 opiate receptor agonists and antagonists, cannabinoid receptor agonists and antagonists, and ESR agonists and antagonists. In addition, the invention provides an isolated nucleic acid molecule that encodes a mu3 opioid receptor, a host cell containing an isolated nucleic acid molecule that encodes a mu3 opioid receptor, and an isolated mu3 opioid receptor polypeptide. Further, the invention provides methods and materials for treating cancers, inflammatory conditions, sepsis conditions, viral infections, and cardiovascular diseases.

The present invention is based on the discovery of a cell surface receptor for estrogen. Specifically, this cell surface receptor for estrogen, designated estrogen surface receptor 1 (ESR1), exhibits ligand specificity for estrogen and 17β-estradiol (E2) as well as E2 conjugated to bovine serum albumen (E2-BSA). In addition, ESR1 is tamoxifen sensitive. In other words, tamoxifen can inhibit the stimulatory effects of ESR1 agonists such as estrogen and E2. Thus, tamoxifen is an ESR1 antagonist. Further, ESR1 is expressed by human endothelial cells. Moreover, the ESR1-mediated biological responses induced by ESR1 agonists include changes in intracellular calcium concentration and nitric oxide release. The existence of a cell surface receptor for estrogen has significant medical implications. For example, plasma membrane impermeable compounds can be used to influence the biological effects of estrogen. Taken together, the discovery of ESR1 and the biological responses mediated by ESR1 provides methods and materials for modulating calcium and nitric oxide regulated mechanisms. As described herein, modulating calcium and nitric oxide regulated mechanisms can be used to treat cancers, inflammatory conditions, sepsis conditions, viral infections, and cardiovascular diseases.

The present invention is also based on the discovery of several assays for identifying mu3 opiate receptor, cannabinoid receptor, or ESR agonists and antagonists. Specifically, the assays involve monitoring at least one biological response induced by mu3 opiate receptors, cannabinoid receptors, or ESRs. Such biological responses include changes in intracellular calcium concentration and nitric oxide release. Thus, the assays can be configured to monitor intracellular calcium concentration, nitric oxide release, or both. The assays are particularly advantageous since the biological responses induced by mu3 opiate receptors, cannabinoid receptors, or ESRs can be detected within seconds of applying an agonist. Thus, many test molecules can be screened rapidly for the ability to either stimulate or inhibit mu3 opiate receptor, cannabinoid receptor, or ESR activities. In addition, the assays are specific for the particular receptor subtype. For example, stimulation or inhibition of mu3 opiate receptor activity can be easily distinguished from effects operating through mu1 or mu2 opioid receptors. Likewise, stimulation or inhibition of CB1 activity can be easily distinguished from effects operating through CB2, and stimulation or inhibition of ESR activity can be easily distinguished from effects operating through the intracellular nuclear receptors for estrogen (e.g., ER-alpha and ER-beta). Further, any results generated from an assay that, for example, monitors intracellular calcium concentration can be easily confirmed by performing an assay that monitors nitric oxide release. Having the ability to confirm a particular test molecule's ability to stimulate or inhibit mu3 opiate receptor, cannabinoid receptor, or ESR activity provides a powerful tool for reliably identifying receptor agonists and antagonists. Taken together, the assays described herein can be used to identify mu3 opiate receptor, cannabinoid receptor, or ESR agonists and antagonists rapidly, specifically, and reliably.

In addition, the present invention is based on the discovery of an isolated nucleic acid molecule that encodes a mu3 opiate receptor. Specifically, the mu3 opiate receptor is a cell surface receptor that exhibits specificity for morphine while being opioid peptide insensitive. In addition, the interaction of morphine with the mu3 opiate receptor induces changes in intracellular calcium concentration and nitric oxide release. Isolated nucleic acid molecules that encode the mu3 opioid receptor, isolated mu3 opioid receptor polypeptides, and host cells containing such isolated nucleic acid molecules are particularly useful to research scientists since these materials allow scientists to explore, for example, the interactions of morphine with the mu3 opiate receptor, the molecular mechanisms by which morphine binding induces intracellular calcium concentration changes, and the relationships of the mu3 opiate receptor with other mu opioid receptors. In addition, these materials can be used to transform mu3 opiate receptor negative cells into mu3 opiate receptor positive cells.

Further, the present invention is based on the discovery of relationships between mu3 opiate receptor, cannabinoid receptor, and ESR activities and various disease conditions. Specifically, disease conditions such as cancer can be treated with specific mu3 opiate receptor, cannabinoid receptor, or ESR antagonists, either individually or in various combinations. In addition, disease conditions such as inflammatory conditions, sepsis conditions, viral infections, and cardiovascular diseases can be treated with specific mu3 opiate receptor, cannabinoid receptor, or ESR agonists, either individually or in various combinations.

In general, the invention features a method for identifying a mu3 opiate receptor agonist. This method involves contacting a cell (e.g., cancer cell) with a test molecule and determining if the test molecule induces a mu3 opiate receptor-mediated response in the cell in a mu3 opiate receptor-specific manner. The cell expresses a mu3 opiate receptor (e.g., a human mu3 opiate receptor) and the test molecule is a molecule other than morphine or dihydromorphine. The determining step can involve monitoring nitric oxide synthase activity in the cell. For example, nitric oxide synthase activity can be monitored by detecting nitric oxide release from the cell. A nitric oxide-specific amperometric probe can be used to detect the nitric oxide release. The determining step can involve monitoring intracellular calcium levels within the cell. For example, a fluorescent ion indicator (e.g., Fura-2) can be used to monitor the intracellular calcium levels. In addition, the determining step can involve monitoring both nitric oxide synthase activity and intracellular calcium levels in the cell.

In another embodiment, the invention features a method for identifying a mu3 opiate receptor antagonist. The method involves contacting a cell (e.g., cancer cell) with a test molecule and a mu3 opiate receptor agonist (e.g., morphine or dihydromorphine), and determining if the test molecule influences (e.g., reduces) induction of a mu3 opiate receptor-mediated response in the cell by the mu3 opiate receptor agonist. The cell expresses a mu3 opiate receptor, and the test molecule is a molecule other than naloxone or naltrexone. The determining step can involve monitoring nitric oxide synthase activity in the cell. For example, nitric oxide synthase activity can be monitored by detecting nitric oxide release from the cell. A nitric oxide-specific amperometric probe can be used to detect the nitric oxide release. The determining step can involve monitoring intracellular calcium levels within the cell. For example, a fluorescent ion indicator (e.g., Fura-2) can be used to monitor the intracellular calcium levels. In addition, the determining step can involve monitoring both nitric oxide synthase activity and intracellular calcium levels in the cell.

Another embodiment of the invention features a method for identifying a cannabinoid receptor agonist. The method involves contacting a cell (e.g., endothelial cell) with a test molecule, and determining if the test molecule induces a cannabinoid receptor-mediated response in the cell in a cannabinoid receptor-specific manner. The cell expresses a cannabinoid receptor (e.g., a human cannabinoid receptor such as CB1), and the test molecule is a molecule other than anandamide. The determining step can involve monitoring nitric oxide synthase activity in the cell. For example, nitric oxide synthase activity can be monitored by detecting nitric oxide release from the cell. A nitric oxide-specific amperometric probe can be used to detect the nitric oxide release. The determining step can involve monitoring intracellular calcium levels within the cell. For example, a fluorescent ion indicator (e.g., Fura-2) can be used to monitor the intracellular calcium levels. In addition, the determining step can involve monitoring both nitric oxide synthase activity and intracellular calcium levels in the cell.

Another embodiment of the invention features a method for identifying a cannabinoid receptor antagonist. The method involves contacting a cell (e.g., endothelial cell) with a test molecule and a cannabinoid receptor agonist (e.g., anandamide), and determining if the test molecule influences (e.g., reduces) induction of a cannabinoid receptor-mediated response in the cell by said cannabinoid receptor agonist. The cell expresses a cannabinoid receptor (e.g., CB1 receptor), and the test molecule is a molecule other than SR 141716A. The determining step can involve monitoring nitric oxide synthase activity in the cell. For example, nitric oxide synthase activity can be monitored by detecting nitric oxide release from the cell. A nitric oxide-specific amperometric probe can be used to detect the nitric oxide release. The determining step can involve monitoring intracellular calcium levels within the cell. For example, a fluorescent ion indicator (e.g., Fura-2) can be used to monitor the intracellular calcium levels. In addition, the determining step can involve monitoring both nitric oxide synthase activity and intracellular calcium levels in the cell.

Another embodiment of the invention features a method for identifying an estrogen surface receptor agonist. The method involves contacting a cell (e.g., endothelial cell) with a test molecule, and determining if the test molecule induces an estrogen surface receptor-mediated response in the cell in an estrogen surface receptor-specific manner. The cell expresses an estrogen surface receptor such as a human estrogen surface receptor. The estrogen surface receptor can be ESR1. The test molecule can be plasma membrane impermeable. The determining step can involve monitoring nitric oxide synthase activity in the cell. For example, nitric oxide synthase activity can be monitored by detecting nitric oxide release from the cell. A nitric oxide-specific amperometric probe can be used to detect the nitric oxide release. The determining step can involve monitoring intracellular calcium levels within the cell. For example, a fluorescent ion indicator (e.g., Fura-2) can be used to monitor the intracellular calcium levels. In addition, the determining step can involve monitoring both nitric oxide synthase activity and intracellular calcium levels in the cell.

Another embodiment of the invention features a method for identifying an estrogen surface receptor antagonist. The method involves contacting a cell with a test molecule and an estrogen surface receptor agonist, and determining if the test molecule influences (e.g., reduces) induction of an estrogen surface receptor-mediated response in the cell by the estrogen surface receptor agonist. The cell expresses an estrogen surface receptor such as a human estrogen surface receptor. The estrogen surface receptor can be ESR1. The test molecule can be plasma membrane impermeable. The estrogen surface receptor agonist can be estrogen, 17β-estradiol, or 17β-estradiol-BSA. The determining step can involve monitoring nitric oxide synthase activity in the cell. For example, nitric oxide synthase activity can be monitored by detecting nitric oxide release from the cell. A nitric oxide-specific amperometric probe can be used to detect the nitric oxide release. The determining step can involve monitoring intracellular calcium levels within the cell. For example, a fluorescent ion indicator (e.g., Fura-2) can be used to monitor the intracellular calcium levels. In addition, the determining step can involve monitoring both nitric oxide synthase activity and intracellular calcium levels in the cell.

In another aspect, the invention features an isolated nucleic acid molecule having first and second nucleic acid sequences. The first nucleic acid sequence is substantially homologous to SEQ ID NO:1, and the second nucleic acid sequence is substantially homologous to SEQ ID NO:2. The first and second nucleic acid sequences are separated by more than about 1500 nucleotides. The isolated nucleic acid molecule can encode a mu3 opiate receptor polypeptide. In addition, the isolated nucleic acid molecule can have a third nucleic acid sequence at least about 80 percent identical to SEQ ID NO:5. The third nucleic acid sequence is located between the first and second nucleic acid sequences.

Another aspect of the invention features a host cell containing an isolated nucleic acid molecule. The isolated nucleic acid molecule has a first and second nucleic acid sequence. The first nucleic acid sequence is substantially homologous to SEQ ID NO:1, and the second nucleic acid sequence is substantially homologous to SEQ ID NO:2. The first and second nucleic acid sequences are separated by more than about 1500 nucleotides.

Another aspect of the invention features an isolated polypeptide having an amino acid sequence at least about 80 percent identical to SEQ ID NO:6. The polypeptide is between 403 and 600 amino acid residues.

Another aspect of the invention features a method for treating a mammal (e.g., human) having cancer. The method involves administering a mu3 opiate receptor antagonist to the mammal such that a mu3 opiate receptor-mediated response is reduced. The reduction of the mu3 opiate receptor-mediated response promotes anti-tumor activity in the mammal. The cancer can be lung cancer, breast cancer, prostate cancer, colon cancer, carcinoma, leukemia, or melanoma. The mu3 opiate receptor-mediated response can be a change in intracellular calcium concentration in a cell (e.g., cancer cell) within the mammal. The mu3 opiate receptor-mediated response can be a change in the amount of nitric oxide released from a cell within the mammal. The method can involve administering a cannabinoid receptor antagonist (e.g., a CB1 receptor antagonist) to the mammal such that a cannabinoid receptor-mediated response is reduced. The method can involve administering an estrogen surface receptor antagonist (e.g., an ESR1 antagonist) to the mammnal such that an estrogen surface receptor-mediated response is reduced. The estrogen surface receptor antagonist can be plasma membrane impermeable, for example, tamoxifen coupled to bovine serum albumin.

In another embodiment, the invention features a method for treating a mammal having cancer. The method involves administering a cannabinoid receptor. antagonist (e.g., a CB1 receptor antagonist) to the mammal such that a cannabinoid receptor-mediated response is reduced. The reduction of the cannabinoid receptor-mediated response promotes anti-tumor activity in the mammal.

Another embodiment of the invention features a method for treating a mammal having cancer. The method involves administering an estrogen surface receptor antagonist (e.g., an ESR1 antagonist) to the mammal such that an estrogen surface receptor-mediated response is reduced. The estrogen surface receptor antagonist is plasma membrane impermeable. In addition, the reduction of the estrogen surface receptor-mediated response promotes anti-tumor activity in the mammal.

Another embodiment of the invention features a method for treating a mammal having an inflammatory condition. The method involves administering a mu3 opiate receptor agonist to the mammal such that a mu3 opiate receptor-mediated response is induced. In addition, the induction of the mu3 opiate receptor-mediated response promotes anti-inflammatory or immunosuppressive activity in the mammal. The inflammatory condition can be arthritis, pericarditis, vasculitis, lupus, bronchitis, or phrenitis. The method can involve administering a cannabinoid receptor agonist to the mammal such that a cannabinoid receptor-mediated response is induced. The method can involve administering an estrogen surface receptor agonist to the mammal such that an estrogen surface receptor-mediated response is induced.

Another embodiment of the invention features a method for treating a mammal having an inflammatory condition. The method involves administering a cannabinoid receptor agonist to the mammal such that a cannabinoid receptor-mediated response is induced. The induction of the cannabinoid receptor-mediated response promotes anti-inflammatory or immunosuppressive activity in the mammal.

Another embodiment of the invention features a method for treating a mammal having an inflammatory condition. The method involves administering an estrogen surface receptor agonist to the mammal such that an estrogen surface receptor-mediated response is induced. The induction of the estrogen surface receptor-mediated response promotes anti-inflammatory or immunosuppressive activity in the mammal.

Another embodiment of the invention features a method for treating a mammal having sepsis. The method involves administering a mu3 opiate receptor agonist to the mammal such that a mu3 opiate receptor-mediated response is induced. The induction of the mu3 opiate receptor-mediated response reduces septic shock in the mammal. The method can involve administering a cannabinoid receptor agonist to the mammal such that a cannabinoid receptor-mediated response is induced. The method can involve administering an estrogen surface receptor agonist to the mammal such that an estrogen surface receptor-mediated response is induced.

Another embodiment of the invention features a method for treating a mammal having sepsis. The method involves administering a cannabinoid receptor agonist to the mammal such that a cannabinoid receptor-mediated response is induced. The induction of the cannabinoid receptor-mediated response reduces septic shock in the mammal.

Another embodiment of the invention features a method for treating a mammal having sepsis. The method involves administering an estrogen surface receptor agonist to the mammal such that an estrogen surface receptor-mediated response is induced. The induction of the estrogen surface receptor-mediated response reduces septic shock in the mammal.

Another embodiment of the invention features a method for treating a mammal having a viral infection (e.g., HIV infection). The method involves administering a mu3 opiate receptor agonist to the mammal such that a mu3 opiate receptor-mediated response is induced. The induction of the mu3 opiate receptor-mediated response promotes an anti-viral response in the mammal. The method can involve administering a cannabinoid receptor agonist to the mammal such that a cannabinoid receptor-mediated response is induced. The method can involve administering an estrogen surface receptor agonist to the mammal such that an estrogen surface receptor-mediated response is induced.

Another embodiment of the invention features a method for treating a mammal having a viral infection. The method involves administering a cannabinoid receptor agonist to the mammal such that a cannabinoid receptor-mediated response is induced. The induction of the cannabinoid receptor-mediated response promotes an anti-viral response in the mammal.

Another embodiment of the invention features a method for treating a mammal having a viral infection. The method involves administering an estrogen surface receptor agonist to the mammal such that an estrogen surface receptor-mediated response is induced. The induction of the estrogen surface receptor-mediated response promotes an anti-viral response in the mammal.

Another embodiment of the invention features a method for treating a mammal having cardiovascular disease. The method involves administering an estrogen surface receptor agonist to the mammal such that an estrogen surface receptor-mediated response is induced. The estrogen surface receptor agonist is plasma membrane impermeable. The induction of the estrogen surface receptor-mediated response can reduce or prevent atherosclerosis in the mammal.

Another embodiment of the invention features a method for treating a mammal with a mu3 opiate receptor agonist such that mu3 opiate receptor-mediated nitric oxide release is suppressed. The method involves administering an opioid receptor agonist to the mammal followed by administering the mu3 opiate receptor agonist. The opioid receptor agonist is not a mu3 opiate receptor agonist. The opioid receptor agonist can be DAMA, β-endorphin, or DAMGO. The mu3 opiate receptor agonist can be morphine or dihydromorphine.

Another aspect of the invention features a pharmaceutical formulation containing a mu3 opiate receptor antagonist and an estrogen surface receptor antagonist.

In another embodiment, the invention features a pharmaceutical formulation containing a mu3 opiate receptor antagonist and a cannabinoid receptor antagonist.

Another embodiment of the invention features a pharmaceutical formulation containing an estrogen surface receptor antagonist and a cannabinoid receptor antagonist.

Another embodiment of the invention features a pharmaceutical formulation containing an estrogen surface receptor antagonist that is membrane impermeable.

Another embodiment of the invention features a pharmaceutical formulation containing a mu3 opiate receptor agonist and an estrogen surface receptor agonist.

Another embodiment of the invention features a pharmaceutical formulation containing a cannabinoid receptor agonist and an estrogen surface receptor agonist.

Another aspect of the invention features the use of a mu3 opiate receptor, cannabinoid receptor, or estrogen surface receptor antagonist in the manufacture of a medicament for the treatment of cancer. The estrogen surface receptor antagonist is plasma membrane impermeable.

In another embodiment, the invention features the use of a mu3 opiate receptor, cannabinoid receptor, or estrogen surface receptor agonist in the manufacture of a medicament for the treatment of an inflammatory condition.

Another embodiment of the invention features the use of a mu3 opiate receptor, cannabinoid receptor, or estrogen surface receptor agonist in the manufacture of a medicament for the treatment of sepsis.

Another embodiment of the invention features the use of a mu3 opiate receptor, cannabinoid receptor, or estrogen surface receptor agonist in the manufacture of a medicament for the treatment of a viral infection.

Another embodiment of the invention features the use of an estrogen surface receptor agonist in the manufacture of a medicament for the treatment of cardiovascular disease. The estrogen surface receptor agonist is plasma membrane impermeable.

Another aspect of the invention features an article of manufacture containing packaging material and a mu3 opiate receptor, cannabinoid receptor, or estrogen surface receptor antagonist contained within the packaging material. The packaging material contains a label or package insert indicating that the mu3 opiate receptor, cannabinoid receptor, or estrogen surface receptor antagonist can be administered to a mammal to treat cancer. The estrogen surface receptor antagonist is plasma membrane impermeable.

In another embodiment, the invention features an article of manufacture containing packaging material and a mu3 opiate receptor, cannabinoid receptor, or estrogen surface receptor agonist contained within the packaging material. The packaging material contains a label or package insert indicating that the mu3 opiate receptor, cannabinoid receptor, or estrogen surface receptor agonist can be administered to a mammal to treat an inflammatory condition.

Another embodiment of the invention features an article of manufacture containing packaging material and a mu3 opiate receptor, cannabinoid receptor, or estrogen surface receptor agonist contained within the packaging material. The packaging material contains a label or package insert indicating that the mu3 opiate receptor, cannabinoid receptor, or estrogen surface receptor agonist can be administered to a mammal to reduce septic shock.

Another embodiment of the invention features an article of manufacture containing packaging material and a mu3 opiate receptor, cannabinoid receptor, or estrogen surface receptor agonist contained within the packaging material. The packaging material contains a label or package insert indicating that the mu3 opiate receptor, cannabinoid receptor, or estrogen surface receptor agonist can be administered to a mammal to treat a viral infection.

Another embodiment of the invention features an article of manufacture containing packaging material and an estrogen surface receptor agonist contained within the packaging material. The packaging material contains a label or package insert indicating that the estrogen surface receptor agonist can be administered to a mammal to treat cardiovascular disease. The estrogen surface receptor agonist is plasma membrane impermeable.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
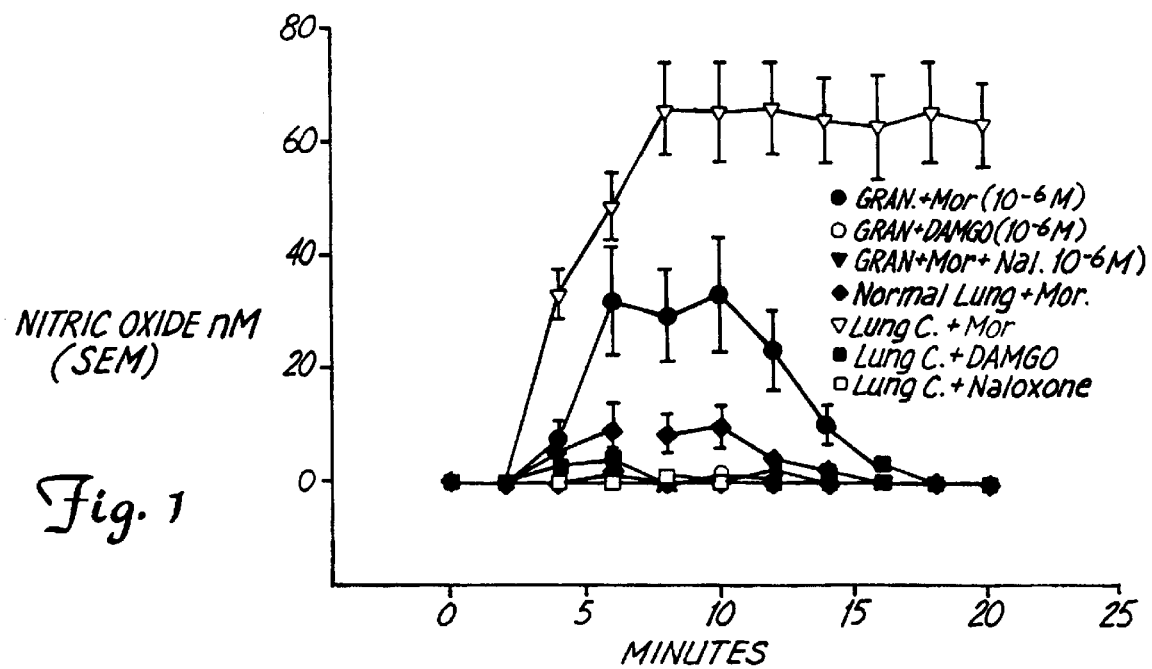
FIG. 1 is a graph plotting NO release verses time for granulocytes, normal lung tissue, and non-small cell lung carcinoma tissue exposed to the indicated compounds.

The invention provides methods and materials for identifying mu3 opiate receptor, cannabinoid receptor, and ESR agonists and antagonists. In addition, the invention provides an isolated nucleic acid molecule that encodes a mu3 opioid receptor, a host cell containing an isolated nucleic acid molecule that encodes a mu3 opioid receptor, and an isolated mu3 opioid receptor polypeptide. Further, the invention provides methods and materials for treating cancers, inflammatory conditions, sepsis conditions, viral infections, and cardiovascular diseases.

Identifying Receptor Agonists

A receptor agonist is any molecule that specifically interacts with a receptor and initiates a biological response mediated by that receptor. For example, an agonist for receptor X can be any molecule that induces an X receptor-mediated response in an X receptor-specific manner. Thus, a mu3 opiate receptor agonist is any molecule that specifically interacts with a mu3 opiate receptor and initiates a mu3 opiate receptor-mediated response. Mu3 opiate receptor-mediated responses include, without limitation, changes in intracellular calcium concentration and nitric oxide release. In addition, a cannabinoid receptor agonist is any molecule that specifically interacts with a cannabinoid receptor and initiates a cannabinoid receptor-mediated response. Cannabinoid receptor-mediated responses include, without limitation, changes in intracellular calcium concentration and nitric oxide release. Further, an ESR agonist is any molecule that specifically interacts with an ESR and initiates an ESR-mediated response. ESR-mediated responses include, without limitation, changes in intracellular calcium concentration and nitric oxide release.

The specificity of the interactions of receptor agonists with mu3 opiate receptors, cannabinoid receptors, and ESRs can be determined using known mu3 opiate receptor, cannabinoid receptor, and ESR antagonists, respectively. For example, a test molecule that induces a biological response that a mu3 opiate receptor mediates can be identified as a mu3 opiate receptor agonist if a mu3 opiate receptor antagonist inhibits the induction of that particular biological response. In addition, the specificity of agonist-receptor interactions can be demonstrated using heterologous expression systems, receptor binding analyses, or any other method that provides a measure of agonist-receptor interaction.

Agonists for a particular receptor can be identified by contacting cells that express that particular receptor with a test molecule, and determining if that test molecule induces a response mediated by that particular receptor in a manner specific for that receptor. For example, a mu3 opiate receptor agonist can be identified by contacting mu3 opiate receptor positive cells with a test molecule, and determining if that test molecule induces a mu3 opiate receptor response in those cells in a mu3 opiate receptor-specific manner. A test molecule can be any molecule having any chemical structure. For example, a test molecule can be a polypeptide, carbohydrate, lipid, amino acid, nucleic acid, fatty acid, steroid. In addition, a test molecule can be lipophilic, hydrophilic, plasma membrane permeable, or plasma membrane impermeable.

The invention provides several assays that can be used to identify receptor agonists. Such assays involve monitoring at least one of the biological responses mediated by a mu3 opiate receptor, cannabinoid receptor, or ESR. As described herein, mu3 opiate receptor-, cannabinoid receptor-, and ESR-mediated responses include, without limitation, increases in intracellular calcium concentration and nitric oxide release. Thus, a mu3 opiate receptor, cannabinoid receptor, or ESR agonist can be identified using an assay that monitors intracellular calcium concentration, nitric oxide release, or both.

Intracellular calcium concentrations can be monitored using any method. For example, intracellular calcium concentrations can be monitored using a dye that detects calcium ions. In this case, cells can be loaded with fura-2, a fluorescent dye, and monitored by dual emission microfluorimetry. The fura-2 loading process can involve washing the cells (e.g., one to four times) with incubation medium lacking calcium. This medium can be balanced with sucrose to maintain osmolarity. After washing, the cells can be incubated (e.g., 30 minutes) with loading solution. This loading solution can contain, for example, 5 µM fura-2/AM and a non-ionic/non-denaturing detergent such as Pluronic F-127. The non-ionic/non-denaturing detergent can help disperse the acetoxymethyl (AM) esters of fura-2. After incubation with the loading solution, the cells can be washed (e.g., one to four times) with, for example, PBS without calcium or magnesium to remove extracellular dye.

Once loaded, the intracellular calcium concentration ($[Ca^{2+}]i$) can be calculated from the fluorescence ratio (340 and 380 nm excitation and 510 nm emission wavelength) according to the following equation: $[Ca^{2+}]i=(R-R_{min}) k_d \beta/(R_{max}-R)$; where R=fluorescence ratio recorded from cell; $R_{min}$=fluorescence ratio of fura-2 free acid recorded in absence of $Ca^{2+}$; $R_{max}$=fluorescence ratio of fura-2 free acid recorded in saturating concentration of $Ca^{2+}$; $k_d$=calcium dissociation constant of the dye; and β=the ratio of fluorescence of fura-2 free acid in the $Ca^{2+}$ free form to the $Ca^{2+}$ saturated form recorded at the wavelength used in the denominator of the ratio. Using an image processing system such as a COMPIX C-640 SIMCA (Compix Inc., Mars, Pa.) system with an inverted microscope, images can be acquired for analysis every 0.4 seconds.

Nitric oxide (NO) release can be monitored directly or indirectly using any method. For example, a NO-specific amperometric probe can be used to measure directly the NO released from cultured cells or tissue fragments as described elsewhere (Stefano GB et al., *J. Biol. Chem.* 270:30290 (1995) and Magazine HL et al., *J. Immunol.* 156:4845 (1996)). Using this NO-specific probe, the concentration of NO gas in solution can be measured in real-time with, for example, a DUO 18 computer data acquisition system obtained from World Precision Instruments. Briefly, the cells or tissue fragments can be placed in a superfusion chamber containing, for example, 2 ML PBS. In addition, a micromanipulator (e.g., a micromanipulator obtained from Zeiss-Eppendorff) can be attached to the stage of an inverted microscope to aid in positioning the amperometric probe 15 µm above the surface of a cell or tissue fragment. Prior to obtaining measurements, the amperometric probe can be calibrated by generating a standard curve using different concentrations of a nitrosothiol donor such as S-nitroso-N-acetyl-DL-penicillamine (SNAP) obtained from Sigma (St. Louis, Mo.). In addition, the amperometric probe can be equilibrated in the same solution (e.g., PBS) used to incubate the cells or tissue fragments during analysis.

Identifying Receptor Antagonists

A receptor antagonist is any molecule that specifically interacts with a receptor and inhibits a receptor agonist from initiating a biological response mediated by that receptor. For example, an antagonist for receptor X can be any molecule that inhibits an X receptor agonist from inducing an X receptor-mediated response in an X receptor-specific manner. Thus, a mu3 opiate receptor antagonist is any molecule that specifically interacts with a mu3 opiate receptor and inhibits a mu3 receptor agonist from initiating a mu3 opiate receptor-mediated response.

An antagonist for a particular receptor can be identified by contacting cells that express that particular receptor with an agonist for that receptor and a test molecule, and determining if that test molecule inhibits the receptor agonist from inducing a response mediated by that particular receptor in a manner specific for that receptor. For example, a mu3 opiate receptor antagonist can be identified by contacting mu3 opiate receptor positive cells with a mu3 opiate receptor agonist such as morphine and a test molecule, and determining if that test molecule inhibits the mu3 opiate receptor agonist from inducing a mu3 opiate receptor response in those cells in a mu3 opiate receptor-specific manner. Again, a test molecule can be any molecule having any chemical structure. For example, a test molecule can be a polypeptide, carbohydrate, lipid, amino acid, nucleic acid, fatty acid, steroid. In addition, a test molecule can be lipophilic, hydrophilic, plasma membrane permeable, or plasma membrane impermeable.

It is to be understood that each of the assays for identifying receptor agonists described herein can be easily adapted such that receptor antagonists can be identified.

Isolated Nucleic Acid Molecules

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisens The term "isolated" as used herein with reference to nucleic acid refers to a naturally-occurring nucleic acid sequence that is not immediately contiguous with both of the sequences with which it is immediately contiguous (one on the 5' end and one on the 3' end) in the naturally-occurring genome of the organism from which it is derived. For example, an isolated nucleic acid molecule can be, without limitation, a recombinant DNA molecule of any length, provided one of the nucleic acid sequences normally found immediately flanking that recombinant DNA molecule in a naturally-occurring genome is removed or absent. Thus, an isolated nucleic acid molecule includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" also includes any non-naturally-occurring nucleic acid sequence since non-naturally-occurring nucleic acid sequences are not found in nature and do not have immediately contiguous sequences in a naturally-occurring genome. For example, non-naturallyoccurring nucleic acid sequences such as engineered nucleic acid sequences are isolated nucleic acid sequences. Engineered nucleic acid sequences can be made using common molecular cloning or chemical nucleic acid synthesis techniques. Isolated non-naturally-occurring nucleic acid sequences can be independent of other sequences or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid sequence can include a nucleic acid molecule that is part of a hybrid or fusion nucleic acid sequence.

An isolated nucleic acid molecule within the scope of the invention is any isolated nucleic acid molecule having a first nucleic acid sequence that is substantially homologous to 5'-GCAGAGGAGAATGTCAGATG-3' (SEQ ID NO:1) and a second nucleic acid sequence that is substantially homologous to 5'-CTAAGCTTGGTGAAGGTCGG-3' (SEQ ID NO:2) separated by more than about 1500 nucleotides (e.g., about 1550, 1600, 1650, 1700, 1750, 1800, 1850, 1900, 1950, 2000, 2050, 2100, or 2150 nucleotides). In other words, more than 1500 nucleotides are located between the first and second nucleic acid sequences. Such isolated nucleic acid molecules can encode polypeptides having the biological characteristics of a mu3 opiate receptor polypeptide as described herein. In addition, the nucleic acid sequence between the first and second nucleic acid sequences can contain a third nucleic acid sequence that is substantially homologous to 5'-GGTACTGGGAAAAC CTCGTGAAGATCTGTG-3' (SEQ ID NO:3) and a fourth nucleic acid sequence that is substantially homologous to 5'-GGTCTCTAGTGTTCTGACGAATTCGAGTGG-3' (SEQ ID NO:4). The third and fourth nucleic acid sequences can be separated by about 400 to about 450 nucleotides (e.g., about 440 nucleotides). Further, the isolated nucleic acid molecules within the scope of the invention can have an internal nucleic acid sequence that is located between the first and second nucleic acid sequences and that is at least about 80 percent identical to 5'-GGTACTGGGA AAACCT-GCTG AAGATCTGTGTTTTCATCTTCGCCTTCATT ATGCCAGTGCTCATCATTACCGTGTGCTATGGACT GATGATCTTGCGCCTCAAGAGTGTCCGCATGC TCTCTGGCTCCAAAGAAAAGGACAGGAATCTTCG AAGGATCACCAGGATGGTGCTGGTGGTGGTGGC TGTGTTCATCGTCTGCTGGACTCCCATTCACATT TACGTCATCATTAAAGCCTTGGTTACAATCCCAGAA ACTACGTTCCAGACTGTTTCTTGGCACTTCTGCAT TGCTCTAGGTTACACAAACAGCTGCCTCAACCC AGTCCTTTATGCATTTCTGGATGAAAACTTCAAAC GATGCTTCAGAGAGTTCTGTATCCCAACCTCTTC CAACATTGAGCAACAAAACTCCACTCGAATTCGT CAGA ACACTAGAGACC-3' (SEQ ID NO:5).

Sequences substantially homologous to a particular sequence (e.g., to SEQ ID NOs:1 and .2) include, without limitation, sequences that hybridize to that particular sequence under high to moderate stringency. High stringency conditions are used to identify nucleic acids that have a high degree of homology or sequence identity to one another. High stringency conditions can include the use of a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% sodium lauryl sulfate (SDS), and 10% dextran sulfate at 42° C., with washes at 42° C. in 0.2×SSC and 0.1% SDS. Alternatively, low ionic strength and high temperature can be employed for washing, for example, 0.015 M NaCl/0.0015 M sodium citrate (0.1× SSC); 0.1% SDS at 65° C.

Moderate stringency conditions are hybridization conditions used to identify nucleic acids that have less homology or identity to one another than do nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060 M NaCl/0.0060 M sodium citrate (4×SSC) and 0.1% SDS can be used at 50° C., with a last wash in 1×SSC, at 65° C. Alternatively, a hybridization wash in 1×SSC at 37° C. can be used.

The isolated nucleic acid molecules described herein can be isolated using any molecular biology technique such as those described by Sambrook J et al. (Molecular Cloning: A Laboratory Manual, 2nd ed., Cold Spring Harbor Laboratory Press (1989)). For example, nucleic acid hybridization or PCR can be used to obtain the isolated nucleic acid molecules described herein.

Host Cells

A host cell within the scope of the invention is any cell containing at least one isolated nucleic acid molecule described herein. Such cells can be prokaryotic and eukaryotic cells. It is noted that cells containing an isolated nucleic acid molecule within the scope of the invention are not required to express them. In addition, the isolated nucleic acid molecule can be integrated into the genome of the cell or maintained in an episomal state. Thus, cells can be stably or transiently transfected with a construct containing an isolated nucleic acid molecule of the invention.

Methods of introducing an isolated nucleic acid molecule into a cell, whether in vivo or in vitro, are well known to those skilled in the art. For example, calcium phosphate precipitation, electroporation, heat shock, lipofection, microinjection, and viral-mediated nucleic acid transfer are common methods of introducing nucleic acid into cells. In addition, naked DNA can be delivered directly to cells in vivo as describe elsewhere (U.S. Pat. No. 5,580,859 and U.S. Pat. No. 5,589,466 including continuations thereof). Further, nucleic acid can be introduced into cells by generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce nucleic acid into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA*, 82:6148 (1985)); gene transfection into embryonic stem cells (Gossler A et al., *Proc Natl Acad Sci USA* 83:9065–9069 (1986)); gene targeting into embryonic stem cells (Thompson et al., *Cell*, 56:313 (1989)); nuclear transfer of somatic nuclei (Schnieke AE et al., *Science* 278:2130–2133 (1997)); and electroporation of embryos (Lo CW, *Mol. Cell. Biol.*, 3:1803–1814 (1983)).

Methods of identifying cells that contain an isolated nucleic acid molecule of the invention are also well known to those skilled in the art. Such methods include, without limitation, PCR and nucleic acid hybridization techniques such as Northern and Southern analysis. In some cases, immunohistochemistry and biochemical techniques can be used to determine if a cell contains a particular isolated nucleic acid molecule by detecting the expression of a polypeptide encoded by that particular molecule.

Isolated Polypeptide

An isolated polypeptide within the scope of the invention is any substantially pure polypeptide having more than about 403 amino acid residues (e.g., about 410, 420, 450, 500, 550, 600, 700, 800, or 900) and an amino acid sequence at least about 80 percent identical to: YWENLLKICVFIFAFIMPV LIITVCYGLMILRLKSVRMLSGSKEKDRNLRRITRM VLVVVAVFIVCWTPIHIYVIIKALVTIPETTFQTVSWH FCIALGYTNSCLNPVLYAFLDENFKRCFREFCIPTSS NIEQQNSTRIRQNTRD (SEQ ID NO:6). For example, such a polypeptide can be between about 403 and 600 amino acid residues. Substantially pure means the preparation contains at least about 60 percent (e.g., about 70, 75, 80, 85, 90, 95, or 99 percent) by weight (dry weight) of the compound of interest (e.g., a mu3 opiate receptor).

Treating Various Disease Conditions

Mammals having cancer can be treated with specific mu3 opiate receptor antagonists, specific cannabinoid receptor antagonists, or specific ESR antagonists, either individually or in various combinations, to inhibit the release of nitric oxide. Inhibiting nitric oxide release can promote anti-tumor activity in mammals having cancers such as lung cancer, breast cancer, prostate cancer, colon cancer, carcinoma, leukemia, or melanoma. Such antagonists can be administered to a mammal at a concentration the specifically inhibits receptor activity. Particular concentrations for individual antagonists can be determined using standard medical and biochemical techniques.

In addition, mammals having disease conditions such as inflammatory conditions (e.g., arthritis, pericarditis, vasculitis, lupus, bronchitis, or phrenitis), sepsis conditions, viral infections (e.g., HIV infections), and cardiovascular diseases can be treated with specific mu3 opiate receptor agonists, specific cannabinoid receptor agonists, or specific ESR agonists, either individually or in various combinations, to increase the release of nitric oxide. Increasing the release of nitric oxide can promote responses that are beneficial to the mammal. For example, nitric oxide release can promote anti-inflammatory and immunosuppressive responses, prevent septic shock, promote anti-viral activity, and reduce or prevent atherosclerosis. Such agonists can be administered to a mammal at a concentration that specifically stimulates receptor activity. Particular concentrations for individual agonists can be determined using standard medical and biochemical techniques.

Receptor agonists or antagonists can be administered by any route including, without limitation, intravenous, intraperitoneal, intramuscular, and oral administrations.

The invention will be further described in the following examples, which do not limit the scope of the invention described in the claims.

EXAMPLES

Example 1

Methods and Materials for mu3 Opiate Receptor Studies

1. Isolation of Human Granulocytes and Tissues

Blood was obtained from the Long Island Blood Services (Melville, N.Y.). Granulocytes were isolated from blood by standard Ficoll-Hypaque separation and the cells resuspended in RPMI medium. Microscopic examination showed a high degree of purity (e.g, about 95 to 97 percent). Tissue specimens, freshly excised lung cancer and thyroid goiter, were obtained from therapy-free patients undergoing surgical treatment. Tissue and cell samples were stored at −70° C. in a guanidine-isothiocyanate solution (4M guanidine isothiocyanate, with 25mM sodium citrate, 0.5% sarcosyl, and 0.1M β-mercaptoethanol) until RNA extraction.

2. RNA Extraction

Total RNA was isolated using a guanidinium thiocyanate-phenol-chloroform method. The integrity of the isolated RNA was confirmed by agarose gel electrophoresis. The RNA samples were treated with DNase I, (RNase free; Boehringer Mannheim) for 30 minutes at 37° C., followed by phenol extraction. The RNA was then precipitated with ethanol and resuspended in water.

3. Oligonucleotide Primers

PCR was performed as a two step reaction with nested primers. The outer primer pair were designed to amplify a 1435 base pair segment of the mu1 receptor (map position 17 to 1452 based on the published 5' and 3' untranslated region; Bare LA et al., *FEBS Lett.* 354:213 (1994)). These outer primers were 5'-GCAGAGGAGAATGTCAGATG-3' (SEQ ID NO:1) and 5'-CTAAGCTTGGTGAAGGTCGG-3' (SEQ ID NO:2). The inner primer pair were esigned to amplify a 440 base pair segment of mu1 (map position 896 to 1336). his segment encodes the third extracellular loop of the mu1 receptor, a region important for mu1 receptor agonist selectivity. The inner primers were 5'-GGTACTGGGAA AACCTCGTGAAGATCTGTG-3' (SEQ ID NO:3) and 5'-GGTCTCTAGTGTTCTGACGAATTCGAGTGG-3' (SEQ ID NO:4). Each oligonucleotide primer was synthesized in an Applied Biosystems 394 DNA/RNA Synthesizer.

4. Reverse-Transcriptase and Polymerase Chain Reaction

Complementary DNA (cDNA) was synthesized from 10 µg of total RNA using an oligo dT primer and 20 U of Avian Myeloblastosis Virus reverse transcriptase (First strand cDNA synthesis kit for RT-PCR, Boehringer Mannheirn) in a reaction volume of 20 µl. A control reaction lacking the reverse transcriptase enzyme also was prepared for each RNA sample and used in PCR analysis to monitor potential DNA contamination. The first round PCR reaction mixture consisted of 1 µM each of the outer primers, ¼ of the RT eaction volume, and 1U Taq Polymerase (Perkin-Elmer). The PCR reaction was run for 35 cycles: 1.5 minutes at 94° C., 1 minute at 56° C., and 2 minutes at 72° C. For the second PCR round, 1 µl of the first round PCR products were added to the 50 µl reaction mix. The conditions were the same as for the first round except that the annealing temperature was changed from 56° C. to 65° C. RT-PCR was performed 5 to 10 times for each sample from different RNA preparations. Reaction mixtures lacking template were used as negative PCR controls. Samples were normalized by the amplification of β-actin.

5. PCR Analysis and Southern Blotting

PCR products were examined by Southern blot analysis. Aliquots (20 µl of the 50 µl PCR reaction) were subjected to gel electrophoresis (1% or 2% agarose gel), stained with ethidium bromide, and blotted onto nylon membranes. PCR products were visualized with a digoxigenin nonradioactive nucleic acid labeling and detection system according to the manufacturer's directions (DIG DNA Labeling Kit and DIG Luminescent Detection Kit for Nucleic Acid, Boehringer Mannheim). Briefly, membranes were prehybridized for 2 hours at 42° C. in DIG-easy Hyb buffer (Boehringer Mannheim). The membrane were then hybridized overnight at 42° C. with a digoxigenin-11-dUTP labeled probe. The probe was a second round PCR product derived from a neuroblastoma cell line. The probe was generated by random primed labeling. Membranes were washed under conditions of low (25° C., 2×SSC, 0.1% SDS, 2 times for 15 minutes each) to high (68° C., 0.1% SSC, 0.1% SDS, 2 times for 15 minutes each) stringency. Signal was detected by chemiluminescence (DIG Luminescent Detection Kit for Nucleic Acid, Boehringer Mannheim) by exposing the membrane to high performance luminescence detection film (Hyperfilm™ ECL, Amersham) for 2–3 hours at room temperature.

6. Sequencing of the Second Round PCR Products

PCR products from the second round amplification were purified with the QIAquick PCR purification kit (QIAGEN) according to the manufacturer's instructions. Purity was assessed by agarose gel electrophoresis and spectrophotometric analysis. Nucleotide sequences of PCR fragments were determined using a dye terminator method (Dye Terminator Cycle Sequencing Kits; Perkin-Elmer) in an Applied Biosystem 370 A DNA Sequencer. Sequence reactions were performed on both strands of template DNA. Results were compared to the mul receptor sequence (Genbank n. L25119).

7. Northern RNA Blotting Analysis

Briefly, 2 $\mu$g of poly $A^+$ RNA for each sample was fractionated in 1% agarose/formaldehyde gel, transferred to nylon membrane, and prehybridized for 2 hours at 50° C. in DIG-easy Hyb buffer (Boehringer Mannheim). The filter was hybridized overnight at 50° C. with the same digoxigenin-11-dDUTP labeled probe used for Southern blot hybridization. Washes were performed under conditions of low (25° C., 2×SSC, 0.1% SDS, 2 times for 15 minutes each) to high (68° C., 0.1% SSC, 0.1% SDS, 2 times for 15 minutes.) stringency. Detection was performed according to manufacturer's instructions (DIG Luminescent Detection Kit for Nucleic Acid, Boehringer Mannheim) and exposure was overnight at room temperature.

8. Opiate Binding Analysis

Binding was studied in human granulocytes, normal lung, and non-small cell lung carcinoma tissue. The separate materials were washed and homogenized in 50 volumes of 0.32 M sucrose (pH 7.4) at 4° C. Membrane suspensions were prepared and the displacement analysis was performed as described in elsewhere (Stefano GB et al, *Proc. Natl. Acad. Sci. USA* 90:11009 (1993); Stefano GB et al., *Proc. Natl. Acad. Sci. USA* 89:9316 (1992); and Stefano GB et al., *J. Biol. Chem.* 270:30290 (1995)). Briefly, aliquots of membrane suspensions from human granulocytes and lung non-small cell carcinoma (less 9% lymphocyte infiltrate) were incubated with non-radioactive compounds at six concentrations for 10 minutes at 22° C. and then with 40 nM of $^3$H-dihydromorphine ([$^3$H]-DHM) for 60 minutes at 4° C. One hundred percent binding is defined as bound [$^3$H]-DHM in the presence of 10 $\mu$M dextrophan minus bound [$^3$H]-DHM in the presence of 10 $\mu$M levorphanol. The $IC_{50}$ values are defined as the concentration of drug that elicits half-maximal inhibition of specific binding. The mean SEM for three experiments is given. The displacement analysis data indicate the potency of various opioid extracts in displacing [$^3$H]-DHM and may give specific information on different receptor populations. Incubation medium for Met-enkephalin contained phosphoramidon (100 $\mu$M) and bestatin (100 $\mu$M) to inhibit enzyme action.

9. Opioid Peptides, Opiates, and Opioid Receptor Antagonists

Mu-selective agonists ([D-Ala$^2$,N-Me-Phe-Gly$^5$(ol)]-enkephalin (DAGO), dihydromorphine, and morphine), delta-selective agonists (enkephalinamide (DAMA), D-Ala-d-Leu-enkephalin (DADLE), Tyr-D-Pen-Gly-Phe-D-Pen (DPDPE), deltorphin, and Met-enkephalin), kappa-selective agonist (dynorphin 1-17), and opioid receptor antagonists (naltrexone and naloxone) were purchased from Sigma.

10. Pathological Examination

Lung (tumor and adjacent normal lung) and thyroid tissue was obtained from resections and either frozen immediately in liquid nitrogen, embedded in optimal cutting temperature, and frozen at −70° C., or formalin fixed and paraffin embedded. Frozen tissue was fixed before staining with 1% paraformaldehyde and stained with hematoxylin and eosin. Lung tissue pathological diagnosis confirmed the presence of poorly differentiated, non-small cell carcinoma with squamoid and clear cell features. Lung not involved with tumor showed edema, other reactive changes, and mild, irregular fibrosis. Lymphocyte infiltration of the tumor was less than 5%. Thyroid tissue showed follicular hyperplasia and random irregular scarring.

11. Direct Measurement of NO Release

A NO-specific amperometric probe (World Precision Instruments, Sarasota, Fla.) was used to measure directly the NO released from granulocytes ($10^7$/ml), normal lung tissue, and non-small cell lung carcinoma tissue (1 mg wet weight) as described elsewhere (Stefano GB et al., *J. Biol. Chem.* 270:30290 (1995) and Magazine HL et al., *J. Immunol.* 156:4845 (1996)). The system was calibrated daily using different concentrations of the nitrosothiol donor S-nitroso-N-acetyl-DL-penicillamine (SNAP; Sigma, St. Louis, Mo.) to generate a standard curve. The concentration of NO gas in solution was measured in real-time with the DUO 18 computer data acquisition system (World Precision Instruments). Each experiment was simultaneously performed with a control (vehicle alone) to exclude experimental drift in NO release unrelated to the administration of compounds. The morphine-stimulated release of NO from granulocytes was demonstrated to be inhibited by naloxone and the NOS inhibitors, N-nitro-L-arginine and N omega-nitro-L-arginine methyl ester (L-NAME).

For cultured endothelial cells (106 cells/chamber), NO release also was measured directly using an NO-specific amperometric probe. Briefly, the cells were placed in a superfusion chamber in 2 mL PBS. A micromanipulator (Zeiss-Eppendorff) attached to the stage of a inverted microscope (Nikon Diaphot) was employed to position the amperometric probe 15 $\mu$m above the cell surface. The system was calibrated daily using different concentration of the nitrosothiol donor S-nitroso-N-acetyl-DL-penicillamine (SNAP; Sigma, St. Louis, Mo.) to generate a standard curve. Baseline levels of NO release were determined by evaluation of NO release in PBS. Cells were stimulated with the respective ligand, and the concentration of NO gas in solution was measured in real-time with the DUO 18 computer data acquisition system (World Precision Instruments). The amperometric probe was allowed to equilibrate for 12 hours in PBS prior to being transferred to the superfusion chamber containing the cells, and manipulation of the cells was performed only with glass instruments. Each experiment was repeated four times. In addition, each experiment was simultaneously performed with a control (vehicle alone) to exclude experimental drift in NO release unrelated to the administration of compounds.

12. Monitoring Intracellular Calcium Levels

Human arterial endothelial cells were purchased from Cell Systems (Eugene, Oregon) and grown at 37° C., 5% $CO_2$ in chamber slides (Nunc Int.) with CS-C medium (Cell Systems) supplemented with 10% fetal calf serum and endothelial growth factor. Intracellular calcium levels were measured by dual emission microfluorimetry using the fluorescent dye fura-2/AM. Cells were loaded with the fluorescent ion indicator as follows. First, the cells were washed twice in incubation medium without calcium, balanced with sucrose to maintain osmolarity (Stefano GB et al., *Science* 213:928–930 (1981)), and then incubated with 5 μM fura-2/AM for 30 minutes at room temperature. The non-ionic and non-denaturing detergent Pluronic F-127 helped disperse acetoxymethyl (AM) esters of fura-2 in the loading buffer. Cells were washed twice with PBS and then test drugs were added. The intracellular calcium concentration ($[Ca^{2+}]i$) was calculated from the fluorescence ratio (340 and 380 nm excitation and 510 nm emission wavelength) according to the following equation: $[Ca^{2+}]i=(R-R_{min})\,k_d\,\beta/(R_{max}-R)$; where R=fluorescence ratio recorded from the cell; $R_{min}$=fluorescence ratio of fura-2 free acid recorded in absence of $Ca^{2+}$; $R_{max}$=fluorescence ratio of fura-2 free acid recorded in saturating concentration of $Ca^{2+}$; $k_d$=calcium dissociation constant of the dye; and β=the ratio of fluorescence of fura-2 free acid in the $Ca^{2+}$ free form to the $Ca^{2+}$ saturated form recorded at the wavelength used in the denominator of the ratio. Images were acquired every 0.4 seconds with an image processing system COMPIX C-640 SIMCA (Compix Inc., Mars, Pa.) and an inverted Nikon, Inc., microscope. Experiments were carried out at room temperature in PBS without calcium/magnesium. Receptor antagonists, when used, were administered 2 minutes prior to the respective agonist.

A two-way ANOVA was used for statistical analysis on the peak $[Ca^{2+}]i$ time, 7 seconds after agonist exposure to the cells. Each experiment was simultaneously performed with up to 6 cells. The mean value was combined with the mean value taken from 4 other replicates. The SEM represents the variation of the mean of the means.

13. Statistical Analysis

Data were evaluated using the Student's t-test. Data acquisition for the direct measurement of NO release was by the computer-interfaced DUO-18 software (World Precision Instruments). The experimental values were then transferred to Sigma-Plot and -Stat (Jandel, San Rafael, Calif.) for graphic representation and evaluation. Data gatherers and were unaware of the experimental treatments.

Example 2 mu3 Opiate Receptor Expression

Nested RT-PCR revealed the presence of a mu-specific mRNA having a sequence different from the mu1 receptor sequence in several tissues. First round PCR amplification using the outer primers (SEQ ID NOs:1 and 2) produced a product of about 1450 base pairs from total RNA isolated from a neuroblastoma cell line (SH-SY5Y cell line). This sequence corresponds to the mu1 receptor sequence (Bare LA et al., *FEBS Lett.* 354:213 (1994)). First round PCR amplification using the outer primers, however, produced a larger product from total RNA isolated from human granulocytes or human lung carcinoma. This larger product was about 2000 base pair (2 kb) and was not detected in human thyroid tissue. Controls included samples without reverse transcriptase to monitor genomic contamination and samples without template to monitor PCR contamination.

Second round PCR amplification confirmed that the first round products were related to a mu-specific sequence. Specifically, second round PCR amplification using the inner primers (SEQ ID NOs:3 and 4) produced a product of about 440 base pairs from the samples having the 1450 base pair product (mu1 receptor) and the 2 kb product (mu3 opiate receptor). It is noted that these inner primers correspond to sequences found on a single exon of the mu1 receptor sequence. Since the 1450 base pair product and the larger 2 kb product each contain a similar 440 base pair fragment, the mRNA transcripts from which these products were derived must contain this exon. Again, controls included samples without reverse transcriptase to monitor genomic contamination and samples without template to monitor PCR contamination.

Southern blot analysis using the second round PCR product from the neuroblastoma cell line as probe confirmed that the 1450 base pair product and the larger 2 kb products contain a similar sequence. Specifically, probe hybridized with the first round PCR products from SH-SY5Y cells (1450 base pair product) as well as lung carcinoma and granulocyte cells (2 kb product). In addition, probe hybridized with 2 kb PCR products produced from colon, rectum, skin, lymphnode, and breast tissue using the outer primer pair. Similar results were obtained using the following cell lines as sources of total RNA: M14, 2–21, 13443 (melanoma), LoVo, LoVo-R-DOX-1 (colon), OVCA 433 (ovary), CCRF-CEM, CEM-VLB 100, K562 (leukemia), MCF-7, MCF-7ADR/R (breast), DU 145, PC3 (prostate), and T24. The 2 kb product, however, was not consistently detected in lymphnode and breast tissue samples. In addition, the larger 2 kb product was not detected in thyroid or cervix tissue. Likewise, it was not detected in the following cell lines: 2–60, CoLo 205, A-2780, A-2780 Cp8, 5637, and RT4. No probe hybridization was detected in lanes containing the PCR controls (samples without reverse transcriptase and samples without template).

Multiple transcripts were detected by Northern blot analysis using the second round PCR product from the neuroblastoma cell line as probe. The 13.5 kb transcript detected by Raynor K et al. (*J. Pharmacol. Exp. Ther.* 272:423 (1995)) in brain tissue was not detected using this probe. Smaller sized transcripts (e.g., 4.5 kb, 2.8 kb, and 1.9 kb), however, were detected. These specific smaller bands were detected in spleen, thymus, prostate, testis, ovary, small intestine, colon, peripheral blood lymphocytes, heart, brain, placenta, liver, skeletal muscle, kidney, and pancreas, but not thyroid.

To determine if the tissues containing the larger 2 kb product express a functional receptor having the pharmacologic properties of a mu3 opiate receptor, the displacement of $[^3H]$-DHM binding with mu, delta, and kappa ligands was examined. None of the tested opioid peptides or analogues exhibited binding affinity for the receptors expressed by granulocytes, lung non-small cell carcinoma cells, or normal lung cells (Table 1). The tested opiate alkaloids, however, did exhibit high binding affinity for the receptors expressed by these cells. In addition, thyroid tissue did not exhibit a mu3 displacement profile. Thus, the presence of the larger 2 kb PCR product correlates with the expression of a functional mu3 opiate receptor. In addition, it is likely that the different pharmacological profiles of mu1 and mu3 opiate receptors are due to alternative splicing.

TABLE 1

Displacement of [$^3$H]-DHM by opioid and non-opioid ligands.

| | IC$_{50}$ nM | | |
|---|---|---|---|
| LIGAND | GRANULOCYTES | LUNG CARCINOMA | NORMAL LUNG |
| Agonists: | | | |
| δ-agonists | | | |
| DAMA | >1000 | >1000 | >1000 |
| Deltorphin | >1000 | >1000 | >1000 |
| Met-enkephalin | >1000 | >1000 | >1000 |
| DADLE | >1000 | >1000 | >1000 |
| DPDPE | >1000 | >1000 | >1000 |
| μ-agonist | | | |
| DAMGO | >1000 | >1000 | >1000 |
| Dihydromorphine | 33 ± 3.9 | 27 ± 4.2 | 28.5 ± 3.3 |
| Morphine | 29 ± 4.5 | 29 ± 3.7 | 28.3 ± 3.1 |
| κ-agonist | | | |
| Dynorphin 1-17 | >1000 | >1000 | >1000 |
| Antagonists: | | | |
| Naltrexone | 30 ± 5.1 | 31 ± 3.8 | 33.4 ± 4.1 |
| Naloxone | 42 ± 4.7 | 40 ± 4.1 | 39.7 ± 3.8 |

DAMA = (D-Ala$^2$, Met$^5$)-enkephalinamide
DADLE = (D-Ala$^2$, Leu$^5$)-enkephalin
DPDPE = (D-Pen$^2$, D-Pen$^5$)-enkephalin
DAMGO = (Tyr-D-Ala$^2$, Gly-N-Me-Phe$^4$, Gly(ol)$^5$)-enkephalin Example 3 mu3 Opiate Receptor Activities

Human granulocytes released NO in response to morphine (1 μM). The NO release was rapid, occurring within 1 minute of exposure. In addition, the NO release was sustained for 10–15 minutes (FIG. 1). Pretreatment with naloxone blocked the morphine-induced NO release. The mu opioid agonist DAMGO had no effect. The effect of morphine on lung carcinoma tissue was similar to that of granulocytes, however, the NO release was instantaneous (i.e., no latency) and sustained for a greater period of time (greater than 20 minutes). Further, the peak level of NO release was significantly greater (35 nM versus 60 nM; P<0.005) for lung carcinoma tissue compared to the human granulocytes. Moreover, the release of NO at peak levels (4–12 minutes post exposure) for human granulocytes and non-small cell lung carcinoma tissue were statistically different (P<0.01). Normal lung tissue exhibited about 10 nM NO release which was less than that exhibited by granulocytes upon morphine exposure. Thyroid did not respond to morphine exposure (1 μM). Each experiment was repeated 4 times and performed with it's own control (vehicle minus drug). The release of NO for these controls was 0.2 nM±1 SEM.

Figure 2:
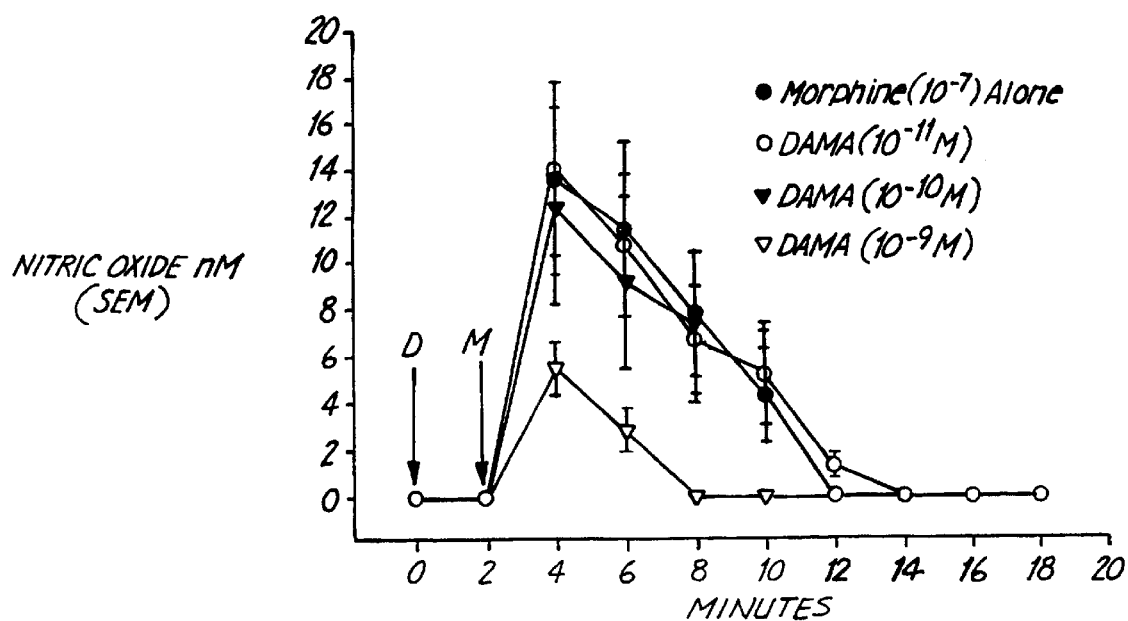
FIG. 2 is a graph plotting NO release verses time for vascular tissue exposed to opioid peptides followed by morphine treatment (100 nM).

Pre-treatment with opioid peptides such as DAMA, β-endorphin, or DAMGO (1 nM) prevented morphine-induced NO release from vascular tissue, human monocytes, and human granulocytes. It is noted that DAMA, β-endorphin, and DAMGO at 1 nM significantly (P<0.05) inhibited morphine-induced NO release from vascular tissue at the 4 to 10 minute time points and each time point was replicated four times. For vascular tissue, morphine alone (100 nM) induced the release of 13.8±4.1 nM NO at 4 minutes (FIG. 2). DAMA (1 nM) alone failed to induce NO release (0.0 nM NO at 4 minutes). DAMA (1 nM) applied two minutes before morphine exposure (100 nM), however, resulted in the release of only 5.2±1.4 nM NO at 4 minutes post morphine exposure. Naltrindole (1 nM) applied two minutes before DAMA (1 nM), which was applied two minutes before morphine exposure (100 nM), resulted in the release of 12.0±3.4 nM NO. Thus, the inhibition of morphine-induced NO release appeared to be mediated by opioid receptors other than the mu3 opiate receptor since naltrindole (1 μM), a delta opioid receptor antagonist, blocked the inhibition of morphine-induced NO release by DAMA.

Figure 3:
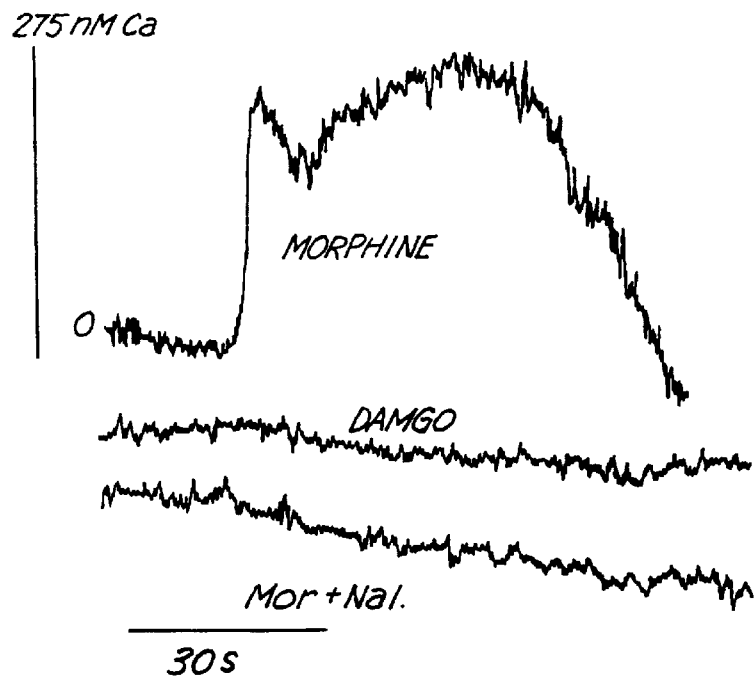
FIG. 3 is a graph plotting real-time intracellular calcium concentration verses time for human arterial endothelial cells treated with morphine (1 $\mu$M), DAMGO (1 $\mu$M), or naloxone (1 $\mu$M) plus morphine (1 $\mu$M).
Figure 4:
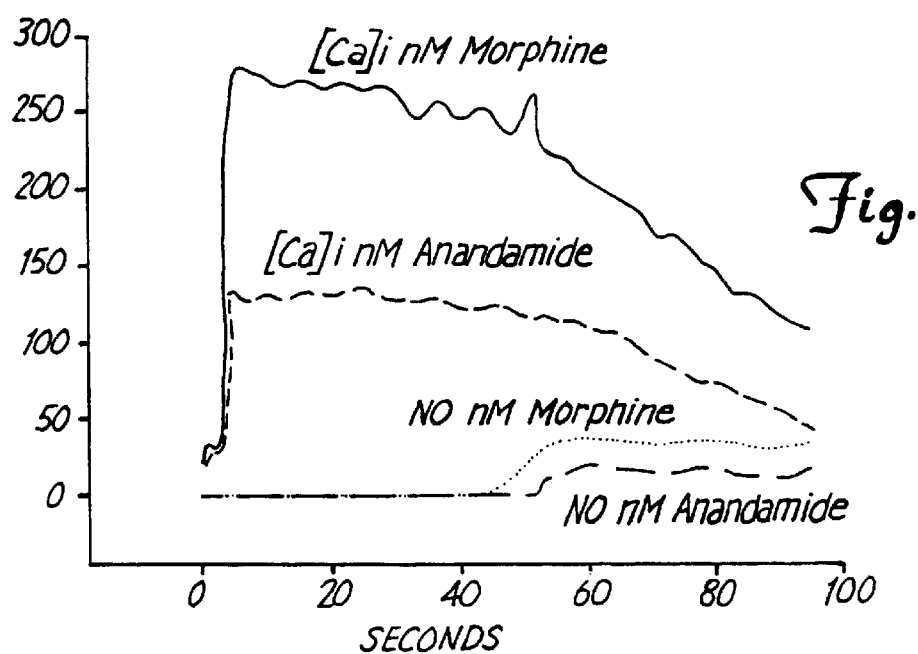
FIG. 4 is a graph plotting real-time intracellular calcium concentration and NO release verses time for human arterial endothelial cells treated with morphine (1 $\mu$M) or anandamide (1 $\mu$M).

Morphine significantly (P<0.001) induced intracellular calcium level increases in a concentration-dependent manner upon administration to endothelial cells (Table 2). In addition, the morphine-induced increase in [Ca$^{2+}$]i was blocked by prior naloxone exposure (1 μM naloxone two minutes prior to morphine exposure). Further, naloxone did not stimulate [Ca$^{2+}$]i at the test concentrations, but did stimulate a non-significant 15% increase at 1 mM. In a representative real-time evaluation of the [Ca$^{2+}$]i stimulated by morphine (1 μM), the observed increase started three seconds after morphine exposure to the endothelial cells (FIG. 3). In part, the three second time period includes the time required for diffusion of the drug to the receptor since it is applied by bath application. The increase in [Ca$^{2+}$]i lasted for about 100–142 seconds (24 measurements) post drug application (FIG. 4). The pseudocolor image assigned by the commercial software revealed bright pink color seven seconds after morphine addition, indicating strong intracellular level increases of calcium. Endothelial cells exposed to naloxone (1 μM) prior to morphine exposure resulted in a general absence of the calcium-Fura-2 pink color at seven seconds similar to that observed for endothelial treated with vehicle only.

TABLE 2

Morphine induced intracellular calcium transients in a concentration dependent and receptor mediated manner.

| Treatment | [Ca$^{2+}$]i nM endothelial cells |
|---|---|
| Control | 31.2 ± 6.7 |
| Morphine (1 μM) | 275.4 ± 21* |
| Morphine (100 nM) | 183 ± 21* |
| Morphine (10 nM) | 96.4 ± 16* |
| Morphine (1 nM) | 38.5 ± 6.6 |
| Morphine + Naloxone (1 μM) | 48.6 ± 14 |

*represents statistically significant at the P < 0.01 level of confidence.

DAMGO (1 μM), a mul and mu2 agonist did not stimulate endothelial [Ca$^{2+}$]i increases (FIG. 3). In addition, DADLE, DAMA, β-endorphin, and dynorphin 1–17 in the concentration range of 1 pM to 1 μM did not stimulate intracellular calcium level increases in the endothelial cells, indicating mu3 opiate receptor mediation.

In cultured human arterial endothelial cells, morphine induced [Ca$^{2+}$]i increases preceded morphine induced NO release by 40±8 seconds (FIG. 4). Morphine addition (1 μM) to the medium resulted in immediate [Ca$^{2+}$]i increase (application at base of the steep increase) that was then followed by a progressive decrease lasting about 2 minutes. About 40 seconds later, an increase in NO release (peak level 36 nM for morphine) occurred which lasted for 10–18 minutes. The raw data were graphed and connected with spline curves so that the precise times could be visualized (FIG. 4). In addition, the increases in [Ca$^{2+}$]i was linked to the increases in NO release. Over a six hour period, the Ca$^{++}$-free incubation medium was changed seven times to leech out intracellular calcium stores. After the six hour incubation, morphine (1 μM) increased $[Ca^{2+}]i$ to 41±3.6. This level is substantially lower than that observed under non-leeching conditions (Table 1). Furthermore, NO release was barely above background in the $Ca^{++}$-leeched endothelial cell following morphine exposure (NO 1.9±0.4 nM compared to a peak value of 33.8±3.9), indicating that intracellular $Ca^{++}$ levels regulate cNOS activity and the calcium originates from mu3 opiate receptor-coupling to $[Ca^{2+}]i$.

In summary, only cells and tissue having the 2 kb PCR product (mu3 splice variant) exhibited a mu3 displacement profile, morphine-induced $[Ca^{2+}]i$ increases, and morphine-induced NO release. For example, thyroid tissue was devoid of the 2 kb PCR product (mu3 splice variant) and lacked opiate binding. In human lung cell carcinoma, the opiate-stimulated NO release was significantly higher and prolonged compared to that observed in granulocytes and normal lung. Further, the morphine-stimulated NO release was inhibited by pre-treatment with opioid peptides having specificity for opioid receptors other than mu3.

It is important to note that in tumors morphine-induced NO release appeared not to be under any feedback regulation. The presence of mu3 opiate receptors on both normal and tumor cells demonstrates the importance of opiates in receptor mediated activities affecting homeostatic mechanisms. In addition, the level and duration of NO release are significantly greater for cancer cells in comparison to normal tissue, indicating the need for a reappraisal of mechanisms involved in opiate tolerance and bioavailability in cancer patients undergoing chronic pain therapy. Moreover, the results presented herein indicate that tumors can use endogenous opiates and NO processes to avoid the response to antigenic challenge. Furthermore, since morphine and related opiate alkaloids are extensively used in chronic cancer therapy, their "new" action must be considered.

As described herein, mu3 opiate receptors are a central target for immunoregulation and inflanunatory responses, with morphine being responsible for the suppression of these functions. Thus, morphine plays a specific role in the modulation of cellular responsiveness to immunostimulating molecules.

Example 4

Cannabinoid Receptor Activities

As described herein, cannabinoid receptors mediate activities similar to the activities mediated by the mu3 opiate receptor. In cultured human arterial endothelial cells loaded with fura 2, both morphine and anandamide induced intracellular calcium transients in a concentration and receptor mediated manner. Further, the calcium transient increase was followed by NO release from these cultured endothelial cells. Thus, rapid signal transduction via intracellular calcium takes place in endothelia in response to both endogenous morphine and cannabinoids.

Anandamide significantly (P<0.001) stimulated endothelial intracellular calcium level increases in a concentration-dependent manner (Table 3). Morphine was found to be more potent than anandamide (P<0.001 at 1 μM to 10 nM). The $[Ca^{2+}]i$ for anandamide stimulation was about half that found for morphine. The $[Ca^{2+}]i$ increase induced by anandamide was blocked by prior exposure to the cannabinoid receptor antagonist SR 171416A (Table 3). Further, SR 171416A did not stimulate $[Ca^{2+}]i$.

TABLE 3

Anandamide induced intracellular calcium transients in a concentration dependent and receptor mediated manner.

| Treatment | $[Ca^{2+}]i$ nM endothelial cells |
|---|---|
| Control | 31.2 ± 6.7 |
| Anandamide (1 μM) | 135 ± 17* |
| Anandamide (100 nM) | 96 ± 14* |
| Anandamide (1 nM) | 34 ± 4.2 |
| Anandamide + SR 141716A | 27.5 ± 5 |

*represents statistically significant at the P < 0.01 level of confidence.

Figure 5:
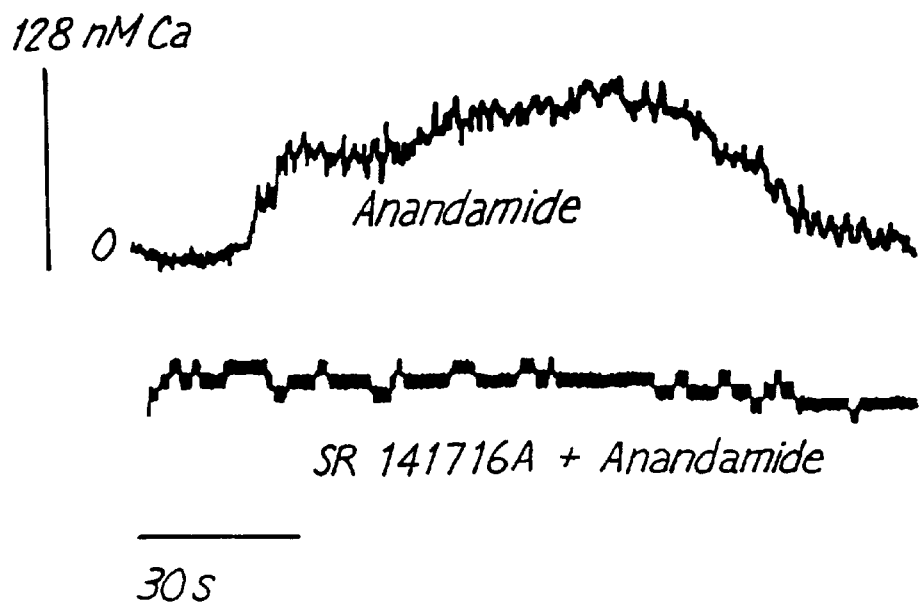
FIG. 5 is a graph plotting real-time intracellular calcium concentration verses time for human arterial endothelial cells treated with anandamide (1 $\mu$M) or SR 141716A (1 $\mu$M) plus anandamide (1 $\mu$M).

Anandamide exposure (1 μM) resulted in $[Ca^{2+}]i$ increases in 3 seconds (FIG. 5). This $[Ca^{2+}]i$ response lasted about 100–142 seconds post drug application (FIG. 4), which was similar to that observed for the morphine induced $[Ca^{2+}]i$ increases operating through mu3 opiate receptors. The pseudocolor image assigned by the commercial software revealed bright pink color seven seconds after anandamide addition, indicating strong intracellular level increases of calcium. Endothelial cells exposed to SR 171416A (1 μM) prior to anandamide exposure resulted in a general absence of the calcium-Fura-2 pink color at seven seconds similar to that observed for endothelial treated with vehicle only.

In cultured human arterial endothelial cells, anandamide induced $[Ca^{2+}]i$ increases preceded anandamide induced NO release (FIG. 4). Anandamide addition (1 μM) to the medium resulted in immediate $[Ca^{2+}]i$ increase (application at base of the steep increase) that was then followed by a progressive decrease lasting about 2 minutes. About 40 seconds later, an increase in NO release (peak level 17 nM for anandamide) occurred which lasted for 10–18 minutes. The raw data were graphed and connected with spline curves so that the precise times could be visualized (FIG. 4). In addition, the increases in $[Ca^{2+}]i$ was linked to the increases in NO release. Over a six hour period, the $Ca^{++}$-free incubation medium was changed seven times to leech out intracellular calcium stores. After the six hour incubation, anandamide (1 μM) increased $[Ca^{2+}]i$ to 36.4±3. This level is substantially lower than that observed under non-leeching conditions (Table 3). Further, NO release was barely above background in the $Ca^{++}$-leeched endothelial cell following anandamide exposure (1.6±06 nM compared to a peak value of 17.9±3.3), indicating that intracellular $Ca^{++}$ levels regulate eNOS activity and the calcium originates from cannabinoid receptor-coupling to $[Ca^{2+}]i$.

In summary, both morphine and anandamide significantly stimulated cultured endothelial intracellular calcium level increases in a concentration-dependent manner in cells preloaded with fura 2/AM. Morphine is more potent than anandamide (approximately 275 vs. 135 nM $[Ca^{2+}]i$) and the $[Ca^{2+}]i$ for both ligands was blocked by prior exposure of the cells to their respective receptor antagonist (naloxone or SR 171416A). Various opioid peptides did not exhibit this ability, indicating a morphine-mu3 opiate receptor mediated process for morphine. In comparing the sequence of events concerning morphine's and anandamide's action in stimulating both $[Ca^{2+}]i$ and NO production in endothelial cells, intracellular calcium concentration increases were found to precede NO release by about 40 seconds. In addition, the opiate and cannabinoid stimulation of $[Ca^{2+}]i$ was attenuated in cells leeched of calcium, indicating that intracellular calcium levels regulate cNOS activity. Further, anandamide stimulated a lower peak level of NO release as well as a lower amount of intracellular calcium mobilization than morphine, indicating the importance of the calcium-NO coupling. Taken together, the present results demonstrate that within 3 seconds of exposure to mu3 opiate receptor or cannabinoid receptor agonists calcium transients are stimulated, lasting about 120 seconds. Thirty to 60 seconds later, following exposure to these agonists, NO release occurs.

Example 5

Methods and Materials for ESR Studies

1. Tissue

Internal thoracic artery (ITA) segments were obtained from patients undergoing elective coronary artery bypass grafting (CABG) for atherosclerotic coronary artery disease. Patients with chronic illnesses, such as diabetes or cancer as well as acute processes (e.g., known infections, trauma), were excluded. In all patients undergoing CABG, the analgesic management included induction with fentanyl (fentanyl citrate adjusted for pH) or sufentanil (N-[-4 (methoxymethyl0-1-[2-(2 thienyl) ethyl]-4-piperidinyl]-N-phenylpropanamide 2 hydroxy- 1,2,3 propanetricaboxylate) up to 15 µg/kg. Maintenance was achieved with the same agents. Parts of ITA that were not used in the CABG procedure were stored in an electrolyte solution at 4° C. (500 mL plasmalyte with 5000 U heparin and 60 mg papaverine). These specimens were immediately transported on ice to the laboratory for processing. Immediately upon arrival, each blood vessel was washed in phosphate buffered saline (PBS) and cut into 3-mm rings. The rings were then cut longitudinally, placed endothelial side up into a superfusion chamber (Bilfinger TV et al., *Ann. Thorac. Surg.* 63:1063–1069 (1997)), and filled with 2 mL of PBS.

2. ESR Agonists and Antagonists

17β-estradiol (E2), E2-conjugated to bovine serum albumin ($E_2$-BSA), 17α-estradiol, and tamoxifen were obtained from Sigma (St. Louis, Mo.) and ICI 182, 780 was obtained from Tocris Cookson Inc. (Ballwin, Mo.). Various concentrations of 17β-estradiol (100 fM to 100 nM) or 17β-estradiol conjugated to bovine serum albumin ($E_2$-BSA) (100 fM to 100 nM of 17β-estradiol) were applied to cultured endothelial cells or ITA fragments to determine a concentration curve. For inhibition studies, the cultured endothelial cells and ITA fragments were stimulated with 17α-estradiol alone (1 nM; n=4); tamoxifen alone (1 nM; n=4); ICI 182, 780 alone (1 nM; n=4); tamoxifen (1 nM) plus 17β-estradiol (1 nM; n=5 4); tamoxifen (1 nM) plus $E_2$-BSA (1 nM; n=4); or ICI 182, 780 (1 nM) plus $E_2$-BSA (1 nM; n=4). In the experiments, tamoxifen and ICI 182, 780 were added to the milieu 5 minutes before 17β-estradiol or $E_2$-BSA.

3. Direct Measurement of NO Release

NO release from the cultured endothelial cells ($10^6$ cells/chamber) and ITA fragments (3 mm rings) placed in a superfusion chamber in 2 mL PBS was measured directly using an NO-specific amperometric probe (World Precision Instruments, Sarasota, Fla.) as described herein. Prior to measuring NO release, the cells were exposed to a concentration gradient of the various ligands. Potential antagonists or the NOS inhibitor, N omega-nitro-L-arginine methyl ester (L-NAME), when used, were administered 5 minutes prior to the various estrogen compounds.

4. Monitoring Intracellular Calcium Levels

Intracellular calcium levels in human arterial endothelial cells were monitored as described herein for the mu3 studies.

Example 6

ESR Activities

Figure 6:
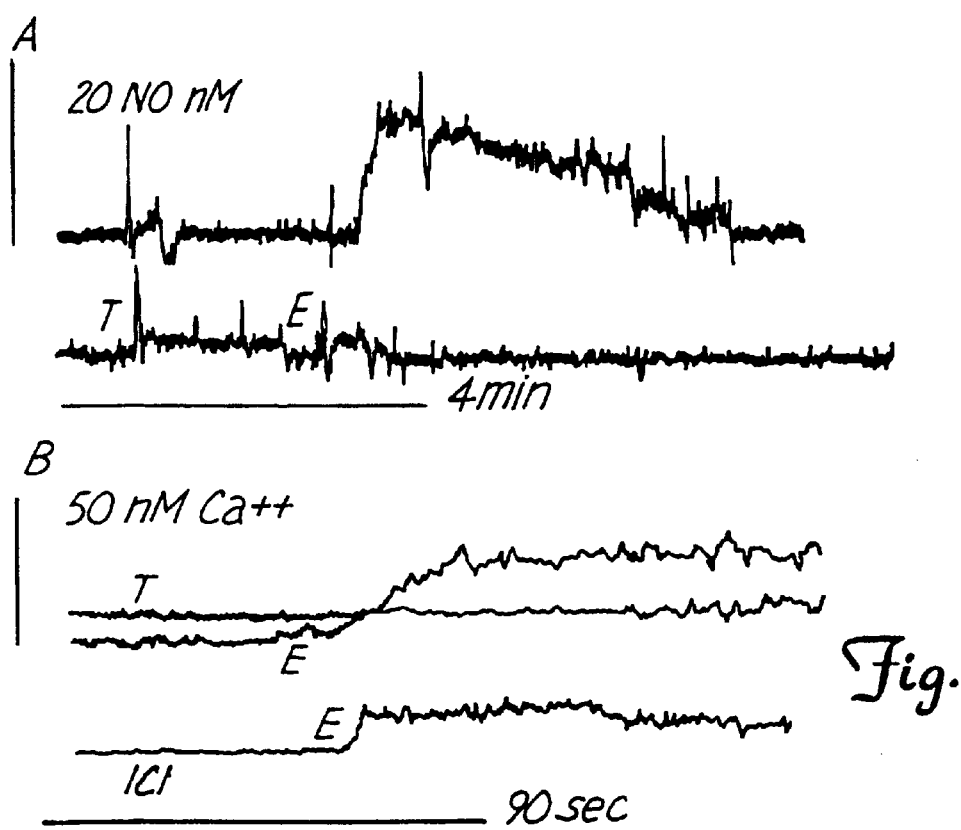
FIG. 6 is a graph plotting real-time nitric oxide release and intracellular calcium concentration verses time for cultured human endothelial cells treated with 17$\beta$-estradiol (E; 1 nM), tamoxifen (T, 1 nM) plus 17$\beta$-estradiol (1 nM), or ICI 182,780 (ICI, 1 nM) plus 17$\beta$-estradiol (1 nM). The curve corresponding to the cells treated first with tamoxifen and then 17$\beta$-estradiol was a straight line raised for better visualization.
Figure 7:
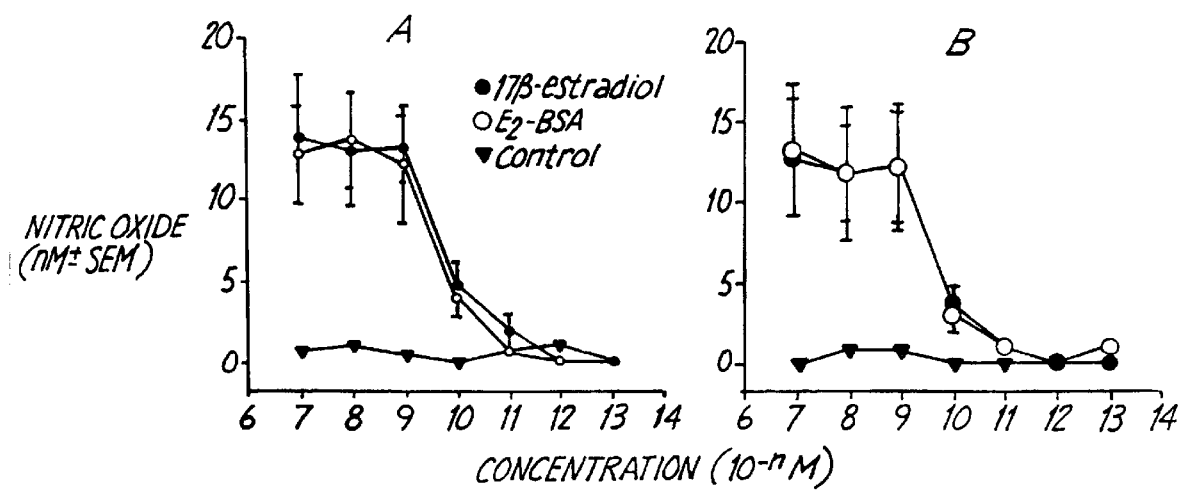
FIGS. 7(A and B) is a graph plotting NO release verses drug concentration for ITA fragments (A) and cultured arterial endothelial cells (B) exposed to 17$\beta$-estradiol, $E_2$-BSA, or vehicle only.

NO release was measured in real-time using a NO-specific amperometric probe following stimulation of the ITA fragments either with 17β-estradiol or $E_2$-BSA. Normally these vessel fragments release low levels of NO (0 to 1 nM NO). In real time, 17β-estradiol (1 nM) stimulated the release of NO (16.1 nM peak value) over a 10 minute time period (FIG. 6A). This 17β-estradiol induced release of NO was inhibited by first exposing the tissue to tamoxifen, an intracellular estrogen receptor blocker. Increasing concentrations of 17β-estradiol (10 pM to 100 nM) resulted in a dose-dependent increase in NO release with a maximal effect observed at 1 nM (FIG. 7). The increase in NO release from both the ITA fragments and the cultured arterial endothelial cells peaked within the 2 minute observation period (FIG. 6). 17β-estradiol at 10 pM failed to stimulate a significant increase in NO release. In addition, 17α-estradiol (1 nM) did not stimulate NO release from either tissue. Tamoxifen (1 nM) significantly diminished ($P<0.005$) the 17β-estradiol-induced increase in endothelial NO release (FIGS. 6 and 8).

Figure 8:
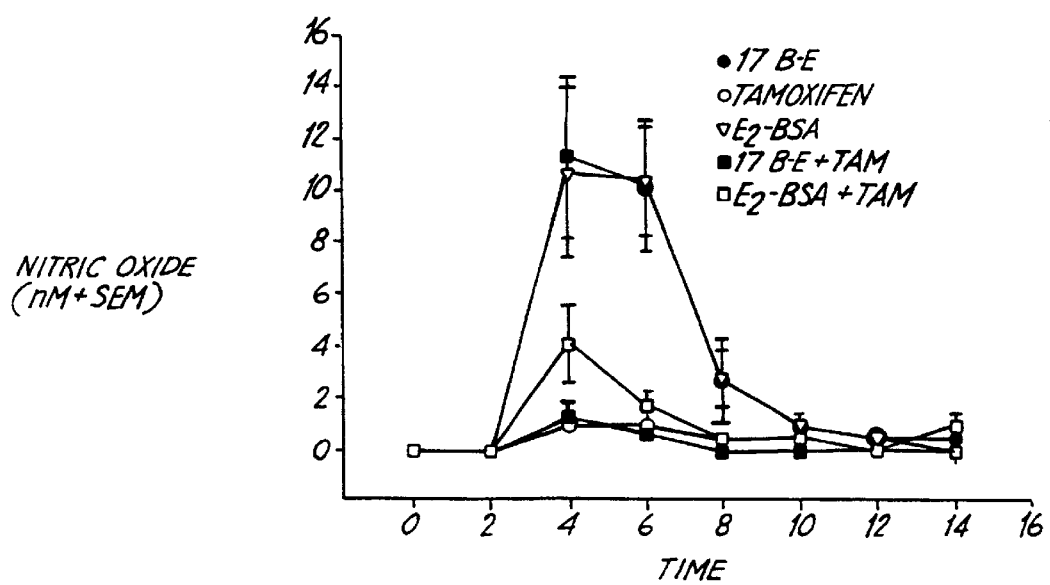
FIG. 8 is a graph plotting nitric oxide release verses time for cultured arterial endothelial cells treated with 17$\beta$-estradiol (17 B-E; 1 nM), tamoxifen (1 nM), E2-BSA (1 nM), 17$\beta$-estradiol (17 B-E; 1 nM) plus tamoxifen (Tam, 1 nM), or E2-BSA (1 nM) plus tamoxifen (1 nM).

Moreover, 17β-estradiol stimulated NO release by interacting with a cell surface receptor, not an intracellular nuclear receptor, since $E_2$-BSA (1 nM) does not penetrate the cellular membrane due to its size yet stimulated NO release from these tissues within 2 minutes of its application (FIG. 8 for cultured endothelial cells; similar results were obtained for the ITA fragments). The $E_2$-BSA induced NO release also was blocked by tamoxifen pre-treatment (FIG. 8). As with 17β-estradiol, the $E_2$-BSA-induced NO release was dose dependent with both the ITA fragments and the cultured arterial endothelial cells (FIG. 8). Addition of $E_2$-BSA at 10 pM to either tissue failed to stimulate a significant increase in NO release. The median effective concentration ($EC_{50}$) for $E_2$-BSA-induced NO release was about 600 pM. Thus, $E_2$-BSA is as potent as 17β-estradiol in stimulating NO release from these tissues (FIG. 7). In addition, gently scraping the ITA to remove the endothelial lining resulted in tissue that was non-responsive to 17β-esterdiol and $E_2$-BSA addition. Thus, these compounds were affecting an estrogen endothelial cell membrane receptor.

Figure 9:
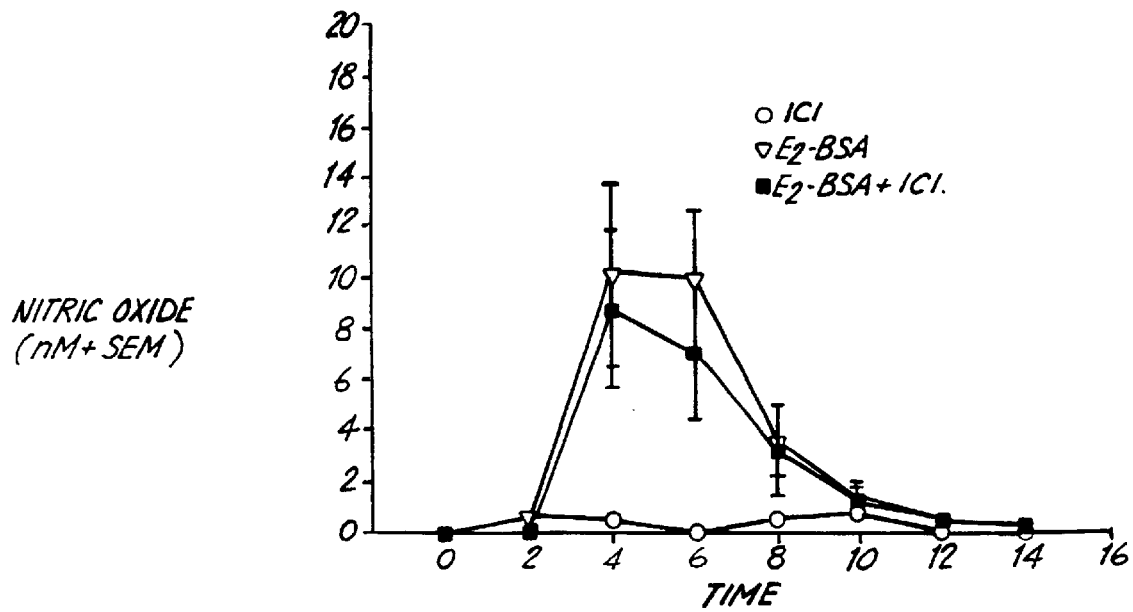
FIG. 9 is a graph plotting nitric oxide release verses time for cultured arterial endothelial cells treated with ICI 182,780 (ICI; 1 nM), E2-BSA (1 nM), or E2-BSA (1 nM) plus ICI 182,780 (1 nM).

Further, a NOS inhibitor, L-NAME (100 µM), blocked the NO release stimulated by 17β-esterdiol or $E_2$-BSA in both the ITA fragments and the cultured arterial endothelial cells (Table 4). Moreover, a nuclear estrogen receptor antagonist, ICI 182, 780 (1 nM), failed to inhibit 17β-esterdiol- or $E_2$-BSA-induced NO release, supporting the cell surface location of the estrogen receptor (FIG. 9 for cultured endothelial cells, similar results were obtained using the ITA fragments).

TABLE 4

L-NAME inhibits estrogen stimulated NO release by inhibiting cNOS activity in endothelial cells.

| Cells | Estrogen agonist (1 nM) | L-NAME (µM) | NO level (nM ± SEM) |
|---|---|---|---|
| Cultured endothelial cells | 17β-estradiol | 0 | 13.8 ± 1.2 |
| Cultured endothelial cells | 17β-estradiol | 100 | 2.3 ± 0.8 |

TABLE 4-continued

L-NAME inhibits estrogen stimulated NO release by inhibiting cNOS activity in endothelial cells.

| Cells | Estrogen agonist (1 nM) | L-NAME ($\mu$M) | NO level (nM ± SEM) |
|---|---|---|---|
| ITA | 17β-estradiol | 0 | 14.6 ± 2.1 |
| ITA | 17β-estradiol | 100 | 2.7 ± 0.9 |

In real time, 17β-esterdiol (1 nM) stimulated a rapid increase in intracellular calcium concentration within six seconds (FIG. 6B). This increase $[Ca^{2+}]i$ was blocked by prior tamoxifen (1 nM) exposure, but not by ICI 182, 780 (1 $\mu$M; FIG. 6B). The $EC_{50}$ value for 17β-estradiol was 500 pM and the $IC_{50}$ value for tamoxifen was 800 pM.

Figure 10:
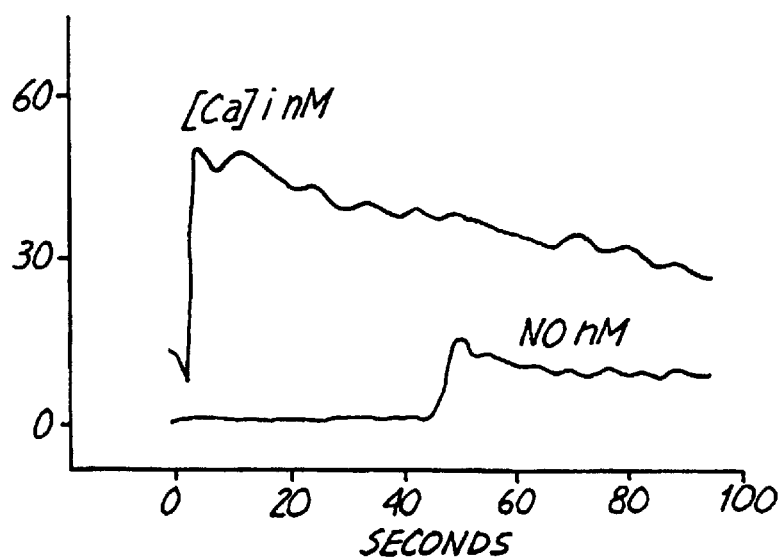
FIG. 10 is a graph plotting real-time intracellular calcium concentration and NO release verses time for cultured human arterial endothelial cells treated with $E_2$-BSA (1 nM).

In comparing the sequence of events concerning $E_2$-BSA's action in stimulating both $[Ca^{2+}]i$ and NO production in the cultured endothelial cells, the increase in $[Ca^{2+}]i$ preceded NO release by 38±9 seconds (from 4 experiments, FIG. 10). The addition of $E_2$-BSA (1 nM) to the medium resulted in an immediate increase in calcium transients (application at base of the steep increase) followed by a progressive decrease lasting about 2 minutes. About 40 seconds later, an increase in NO release (peak level 18 nM for $E_2$-BSA) occurred, lasting for about 10 minutes.

Further, over a 3 hour period, the $Ca^{++}$ free incubation medium was changed six times to leach out intracellular calcium stores. After the 3 hour incubation, 17β-estradiol (1 nM) increased $[Ca^{2+}]i$ to 3.8±0.6. This level was substantially lower than the level observed under non-leaching conditions (FIG. 6). Further, NO release was barely above background in the $Ca^{++}$-leached endothelial cell following 17β-estradiol exposure (NO 1.8±0.6 nM compared to a peak value of 16.0±2.7), indicating that intracellular $Ca^{++}$ levels regulate cNOS activity and that $Ca^{++}$ originates from ESR's coupling to $[Ca^{2+}]i$.

In summary, 17β-estradiol exposure to ITA endothelia and arterial endothelia in culture stimulated NO release within seconds in a concentration-dependent manner whereas 17α-estradiol had no effect. 17β-estradiol conjugated to bovine serum albumin ($E_2$-BSA) also stimulated NO release, indicating mediation by a cell surface receptor. Tamoxifen, an intracellular estrogen receptor inhibitor, antagonized the action of both 17β-estradiol and $E_2$-BSA, whereas ICI 182,780, another selective inhibitor of the intracellular nuclear estrogen receptor had no effect. Thus, tamoxifen is an antagonist of ESR1 and ICI 182,780 is not. In addition, 17β-estradiol stimulated release of endothelial NO in a manner dependent on the initial stimulation of intracellular calcium transients. The effect of 17β-estradiol on endothelial NO release was abolished by leaching out the intracellular calcium stores, or by the addition of a cNOS inhibitor, L-NAME. These results indicate that a physiological dose of estrogen can acutely stimulate NO release from human endothelial cells via the activation of an ESR that is coupled to increases in intracellular calcium. This cNOS-derived NO, in turn, can induce a hyperpolarization of the artery's smooth muscle cells leading to vasodilatation via myogenic tone reduction.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying an estrogen surface receptor agonist, said method comprising:
   a) contacting a cell with a test molecule wherein said cell expresses an estrogen surface receptor, and
   b) determining if said test molecule induces an estrogen surface receptor-mediated response in said cell in an estrogen surface receptor-specific manner, wherein induction of said estrogen surface receptor-mediated response in said cell in said estrogen surface receptor-specific manner is inhibited by tamoxifen, is not inhibited by ICI 182,780, and indicates that said test molecule is said estrogen surface receptor agonist.

2. The method of claim 1, wherein said cell is an endothelial cell.

3. The method of claim 1, wherein said estrogen surface receptor is a human estrogen surface receptor.

4. The method of claim 3, wherein said estrogen surface receptor is ESR1.

5. The method of claim 1, wherein said test molecule is plasma membrane impermeable.

6. The method of claim 1, wherein said determining step comprises measuring nitric oxide release from said cell.

7. The method of claim 1, wherein said determining step comprises measuring intracellular calcium levels within said cell.

8. The method of claim 1, wherein said determining step comprises measuring nitric oxide release from said cell and measuring intracellular calcium levels in said cell.

9. A method for identifying an estrogen surface receptor agonist, said method comprising:
   a) contacting a cell with a test molecule, wherein said cell expresses an estrogen surface receptor, and
   b) determining if said test molecule induces an estrogen surface receptor-mediated response in said cell in an estrogen surface receptor-specific manner, wherein induction of said estrogen surface receptor-mediated response in said cell in said estrogen surface receptor-specific manner is inhibited by tamoxifen, occurs when a membrane impermeable form of said test molecule is used, and indicates that said test molecule is said estrogen surface receptor agonist.

10. The method of claim 9, wherein said cell is an endothelial cell.

11. The method of claim 9, wherein said estrogen surface receptor is a human estrogen surface receptor.

12. The method of claim 11, wherein said estrogen surface receptor is ESR1.

13. The method of claim 9, wherein said determining step comprises measuring nitric oxide release from said cell.

14. The method of claim 9, wherein said determining step comprises measuring intracellular calcium levels within said cell.

15. The method of claim 9, wherein said determining step comprises measuring nitric oxide release from said cell and measuring intracellular calcium levels in said cell.

* * * * *